(12) United States Patent
Johnson

(10) Patent No.: US 10,751,249 B2
(45) Date of Patent: Aug. 25, 2020

(54) TRIGGER POINT DRY NEEDLING IN MOTION AND METHOD OF USE

(71) Applicant: Johnson Athletic Advantage LLC, Allen, TX (US)

(72) Inventor: Cody Johnson, Allen, TX (US)

(73) Assignee: Johnson Athletic Advantage LLC, Allen, TX (US)

(*) Notice: Subject to any disclaimer, the term of this patent is extended or adjusted under 35 U.S.C. 154(b) by 283 days.

(21) Appl. No.: 15/822,176

(22) Filed: Nov. 26, 2017

(65) Prior Publication Data
US 2019/0159965 A1 May 30, 2019

(51) Int. Cl.
| | | |
|---|---|---|
| *A61H 39/02* | (2006.01) | |
| *A61H 39/08* | (2006.01) | |
| *A61B 5/00* | (2006.01) | |
| *A61H 39/00* | (2006.01) | |
| *A61B 5/11* | (2006.01) | |

(52) U.S. Cl.
CPC .......... *A61H 39/02* (2013.01); *A61B 5/4854* (2013.01); *A61H 39/007* (2013.01); *A61H 39/08* (2013.01); *A61H 39/086* (2013.01); *A61B 5/1107* (2013.01); *A61B 5/1123* (2013.01); *A61B 5/4824* (2013.01); *A61H 2201/1664* (2013.01); *A61H 2201/1671* (2013.01); *A61H 2230/00* (2013.01)

(58) Field of Classification Search
CPC ..... A61B 5/1107; A61B 5/4824; A61H 39/08; A61H 39/083; A61H 39/086; A61N 5/0619
See application file for complete search history.

(56) References Cited

U.S. PATENT DOCUMENTS

| | | | |
|---|---|---|---|
| 4,716,898 A | 1/1988 | Chauve et al. | |
| 6,022,368 A | 2/2000 | Gavronsky et al. | |
| 6,395,291 B1* | 5/2002 | Isacsson | A61K 31/445 424/400 |
| 6,808,499 B1 | 10/2004 | Churchill et al. | |
| 7,200,444 B2 | 4/2007 | Gavronsky et al. | |
| 7,267,655 B1 | 9/2007 | Lyapko | |
| 2006/0095087 A1 | 5/2006 | Shin | |

(Continued)

FOREIGN PATENT DOCUMENTS

| | | |
|---|---|---|
| CN | 2539509 | 3/2003 |
| CN | 102846466 | 4/2014 |

(Continued)

OTHER PUBLICATIONS

Ries, Eric "Dry Needling: Getting to the Point", APTA, apta.org, May 2015. http://www.apta.org/PTinMotion/2015/5/DryNeedling/.

(Continued)

*Primary Examiner* — Thomas McEvoy
(74) *Attorney, Agent, or Firm* — Schultz & Associates, P.C.

(57) ABSTRACT

A method is provided for a novel application of trigger point dry needling. A target tissue is identified based on the observation of a series of movement patterns performed by the patient. Once identified, a needle movement protocol is used to insert a needle into the target tissue to a myofascial trigger point during one or more movement patterns. The needle protocol is adjusted until a local twitch response is induced.

21 Claims, 35 Drawing Sheets

(56) References Cited

U.S. PATENT DOCUMENTS

| | | | |
|---|---|---|---|
| 2009/0281468 A1 | 11/2009 | Xu | |
| 2010/0087762 A1 | 4/2010 | Herbert | |
| 2011/0306999 A1 | 12/2011 | Lam et al. | |
| 2014/0128899 A1 | 5/2014 | Shin | |

FOREIGN PATENT DOCUMENTS

| | | |
|---|---|---|
| CN | 102846465 | 8/2014 |
| KR | 100718647 | 5/2007 |
| RU | 2182819 | 5/2002 |
| RU | 2300400 | 6/2007 |
| TW | 201204340 | 2/2012 |
| WO | 2016056335 | 4/2016 |

OTHER PUBLICATIONS

Unverzagt et al, "Dry Needling for Myofascial Trigger Point Pain: A Clinical Commentary", International Journal of Sports Physical Therapy, vol. 10, No. 3 (Jun. 2015): pp. 402-418.

SFMA Worksheets available at https://www.functionalmovement.com/files/articles/463a_sfma-version11-2015-flowcharts.pdf (undated) last accessed Feb. 23, 2018.

"Dry Needling/Intramuscular Manual Therapy," Back in Action, biaphysicaltherapy.com Jul. 28, 2016. https://web.archive.org/web/20160730171434/http://biaphysicaltherapy.com:80/dry-needling-intramuscular-manual-therapy/.

* cited by examiner

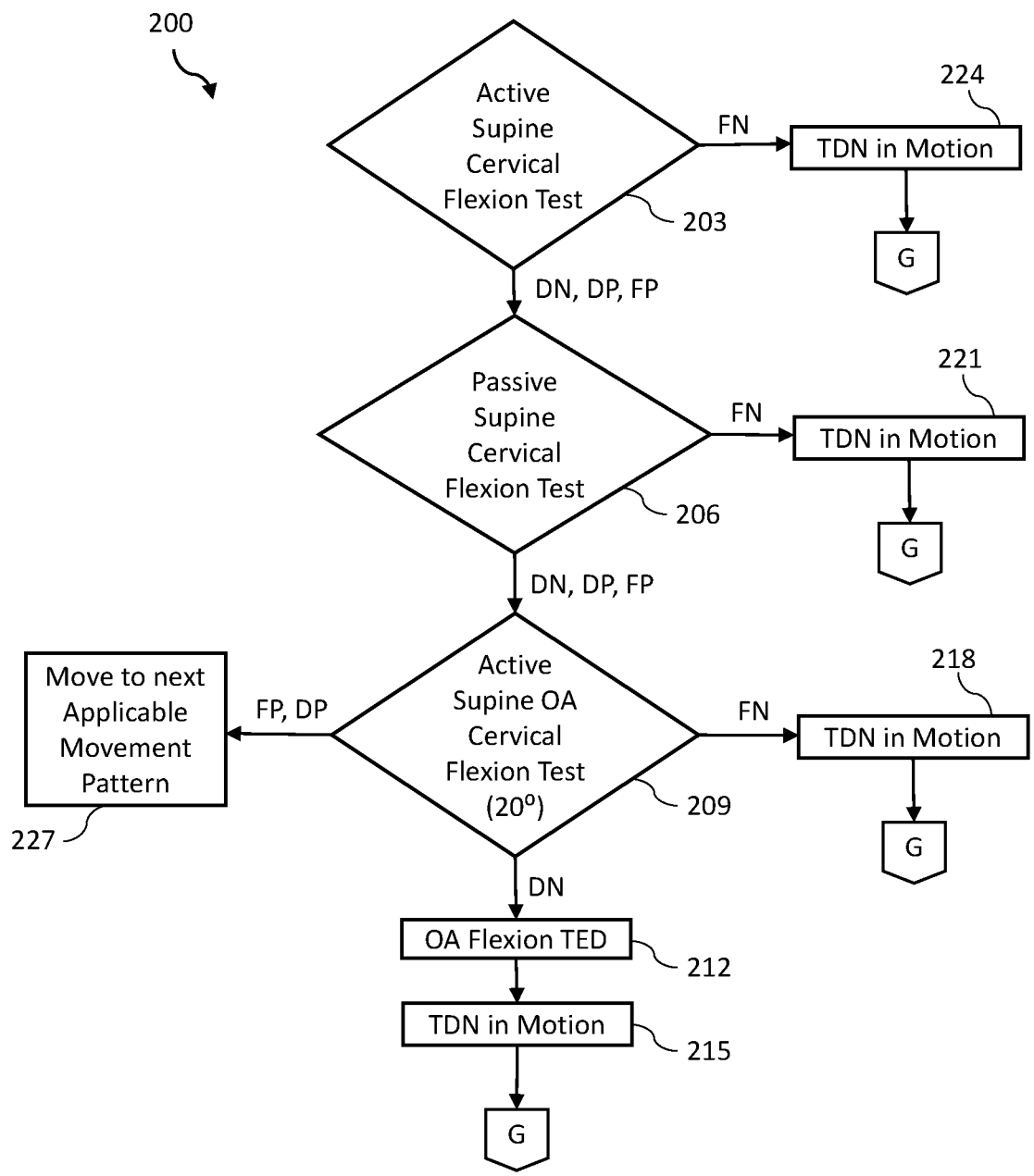
Figure 2A-Cervical Spine

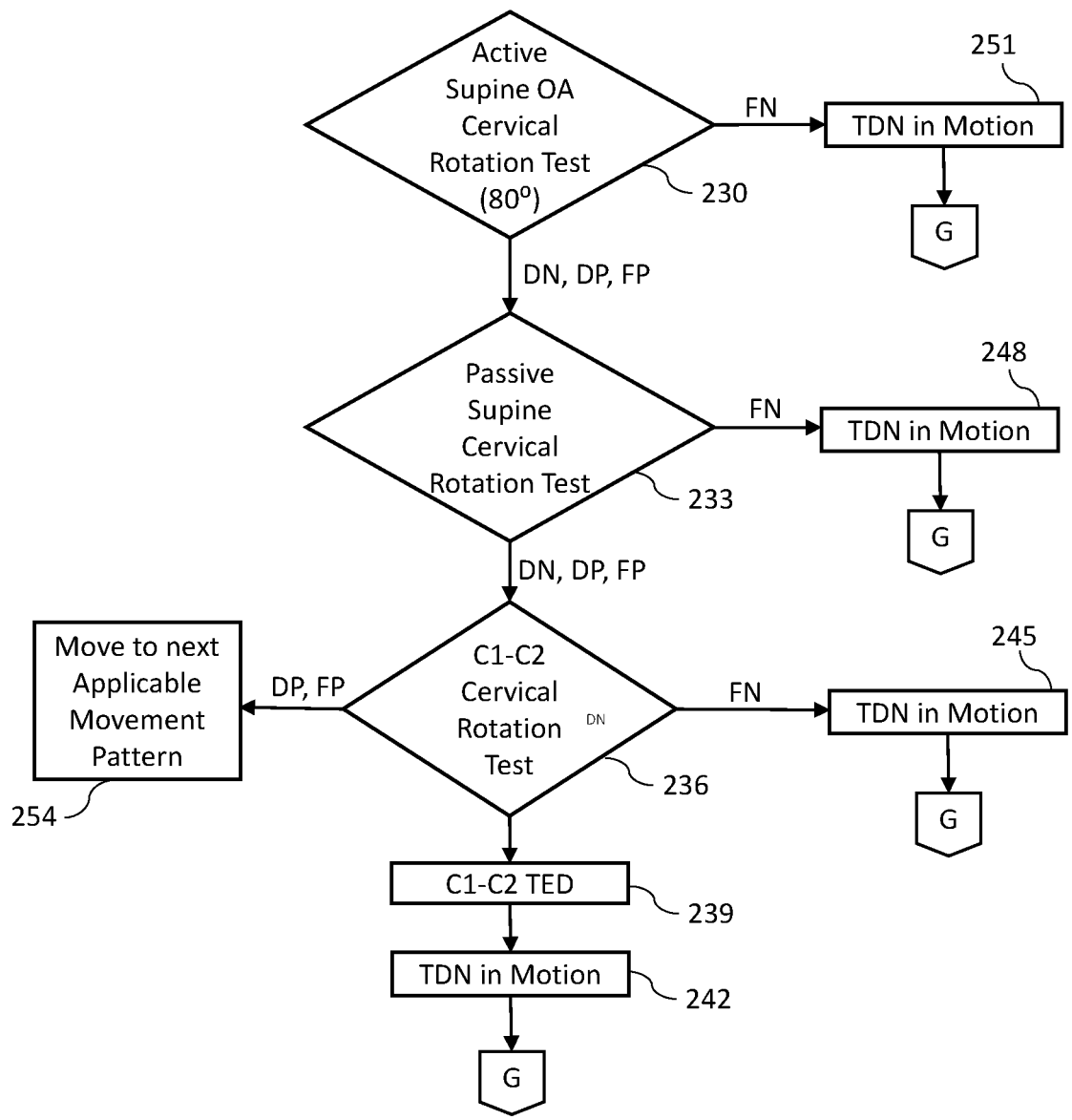
Figure 2B-Cervical Spine

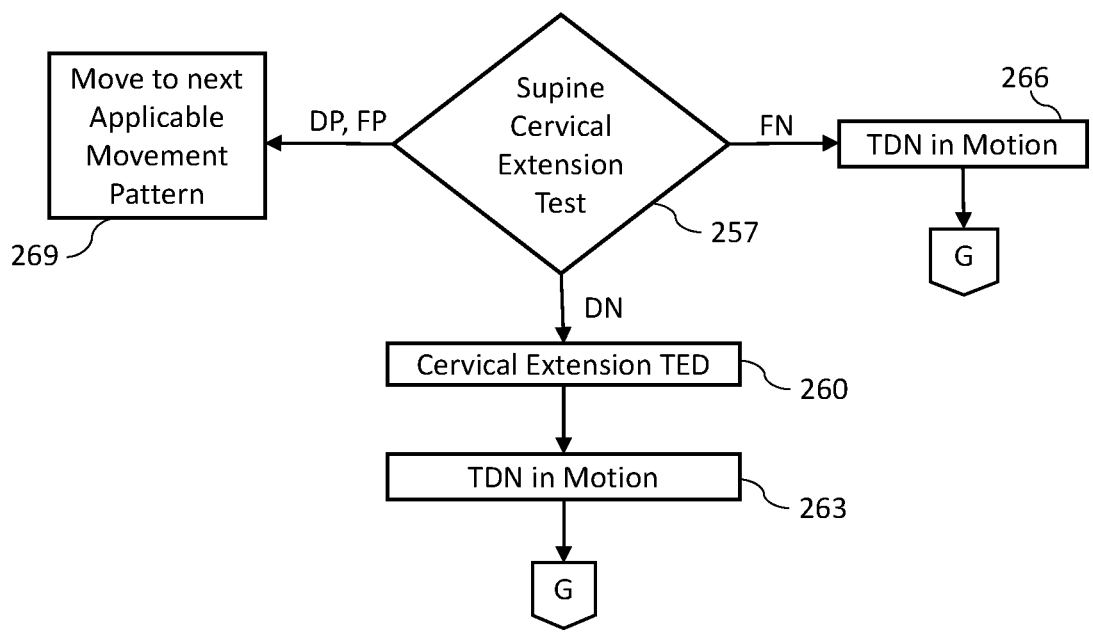
Figure 2C-Cervical Spine

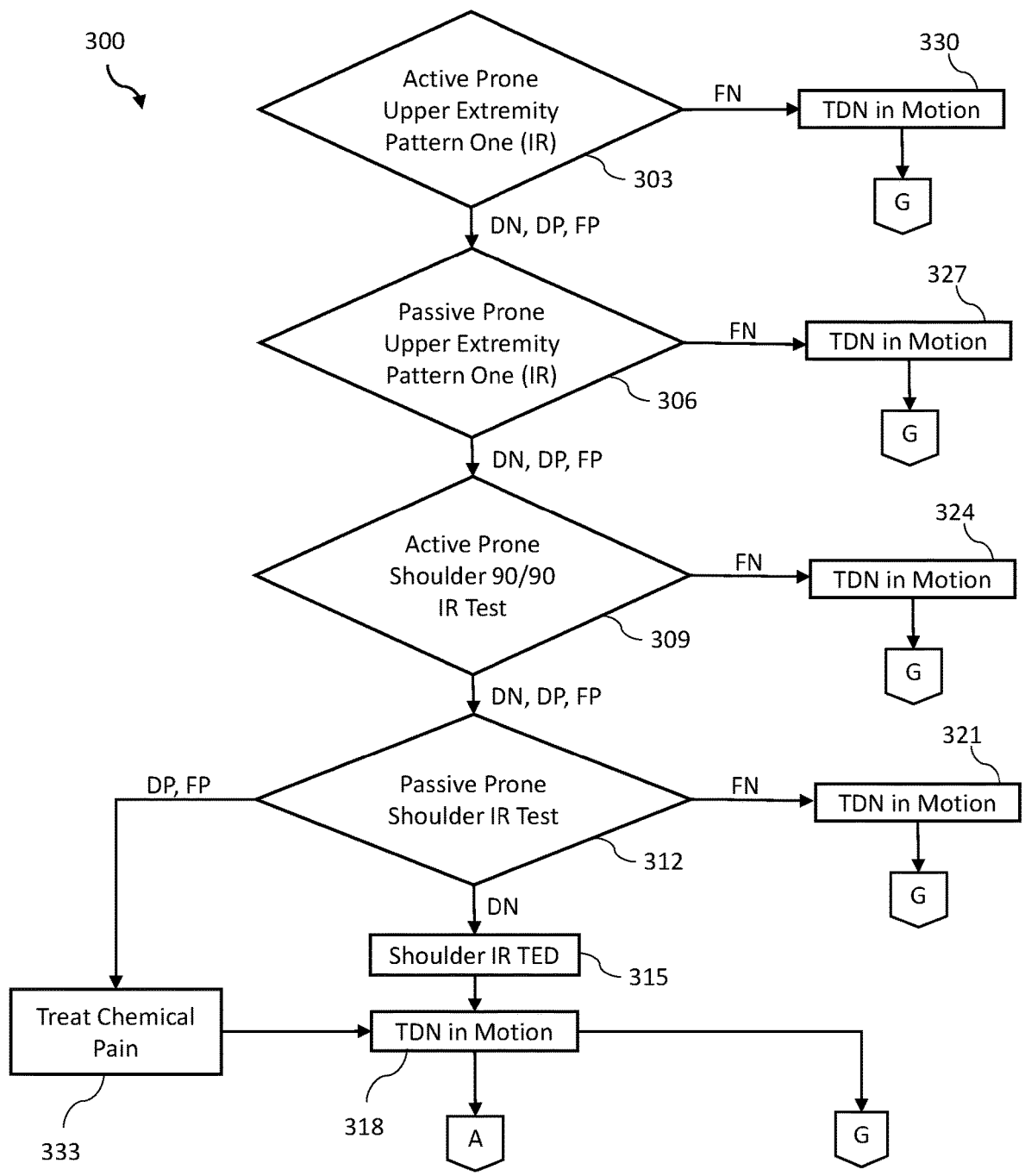
Figure 3A-Limited Upper Extremity Pattern 1

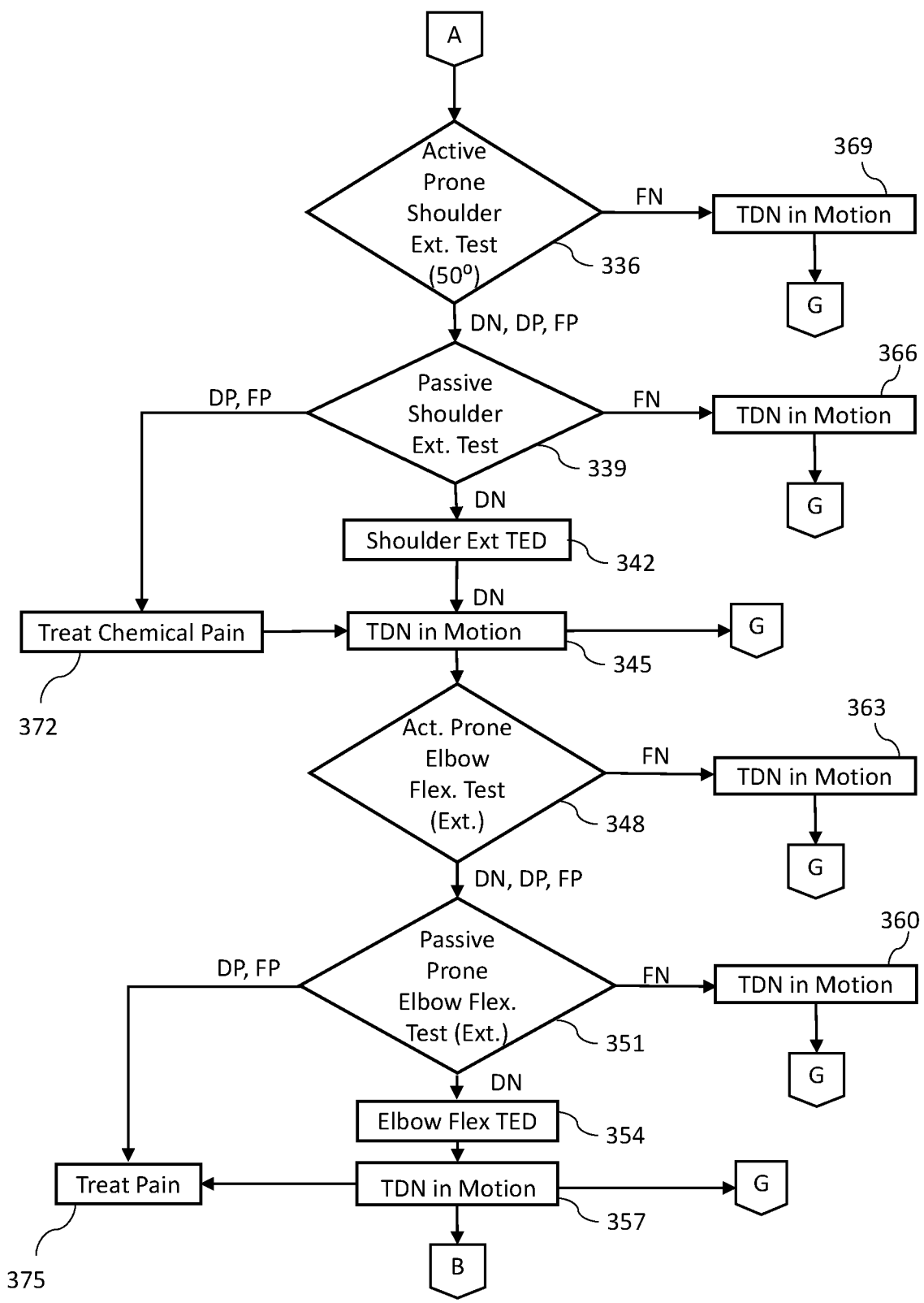
Figure 3B-Limited Upper Extremity Pattern 1

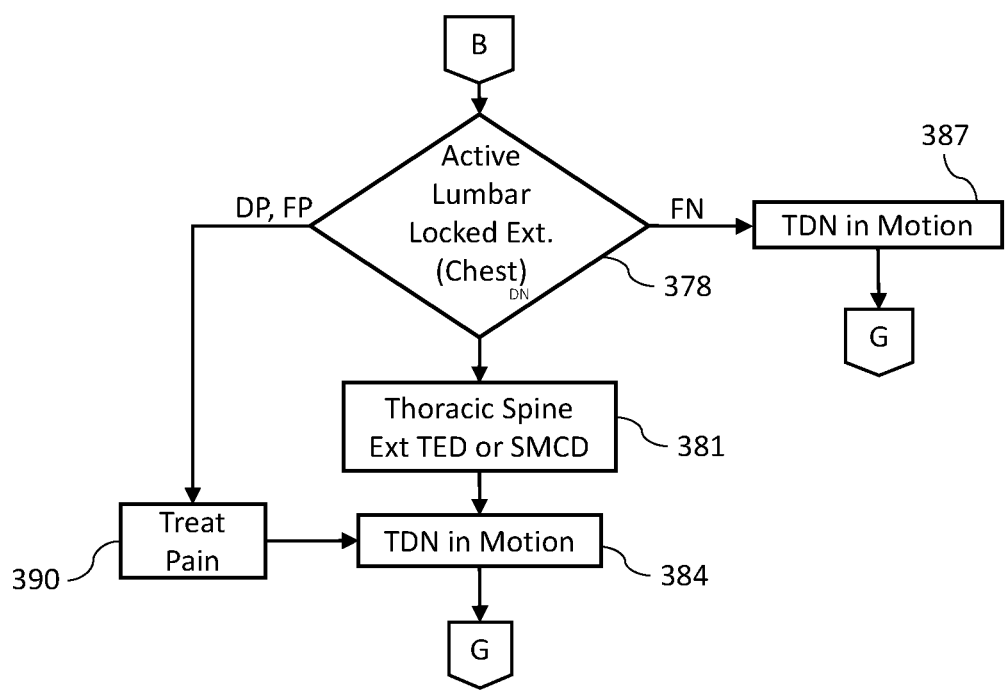
Figure 3C-Limited Upper Extremity Pattern 1

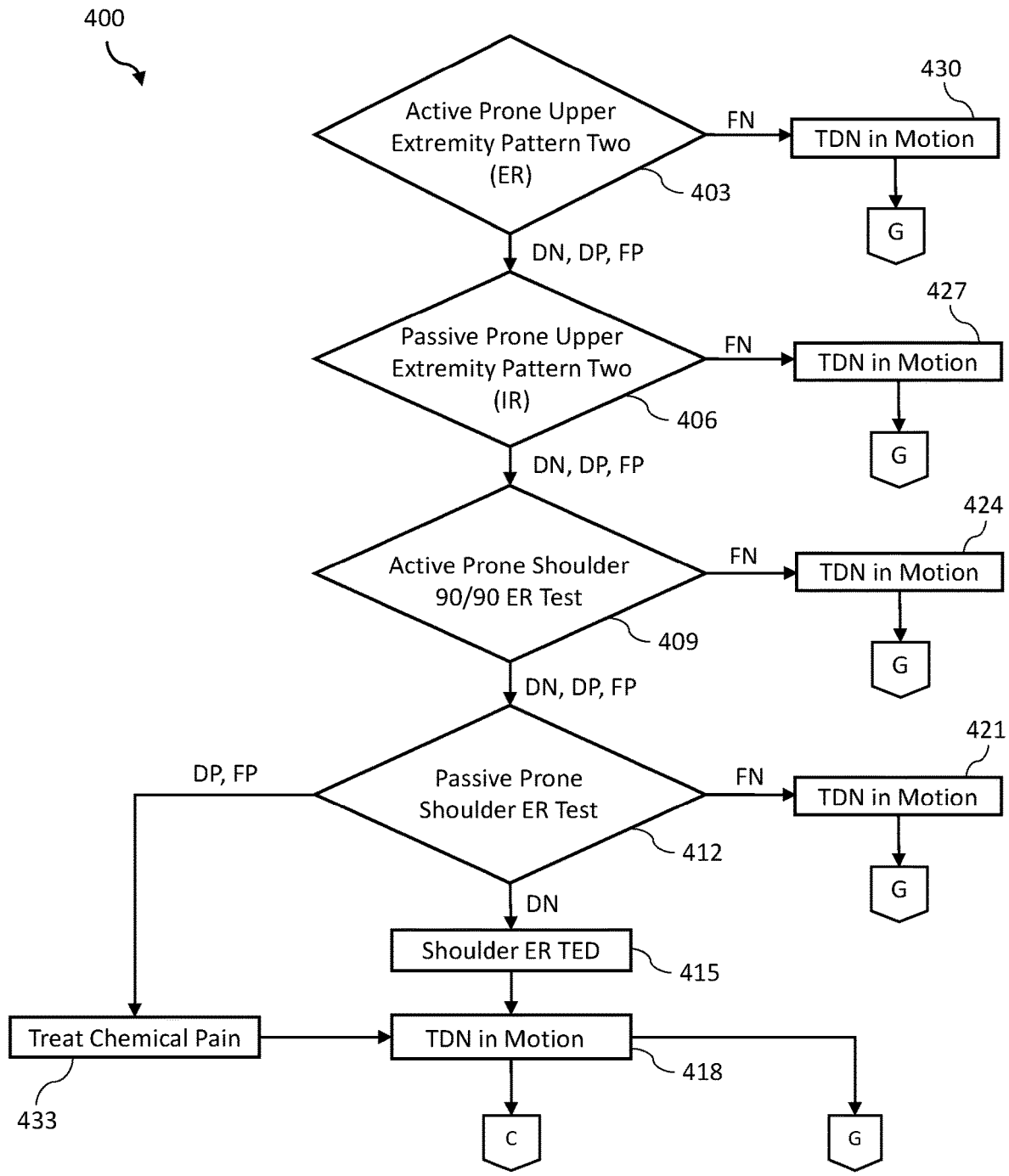
Figure 4A-Limited Upper Extremity Pattern 2

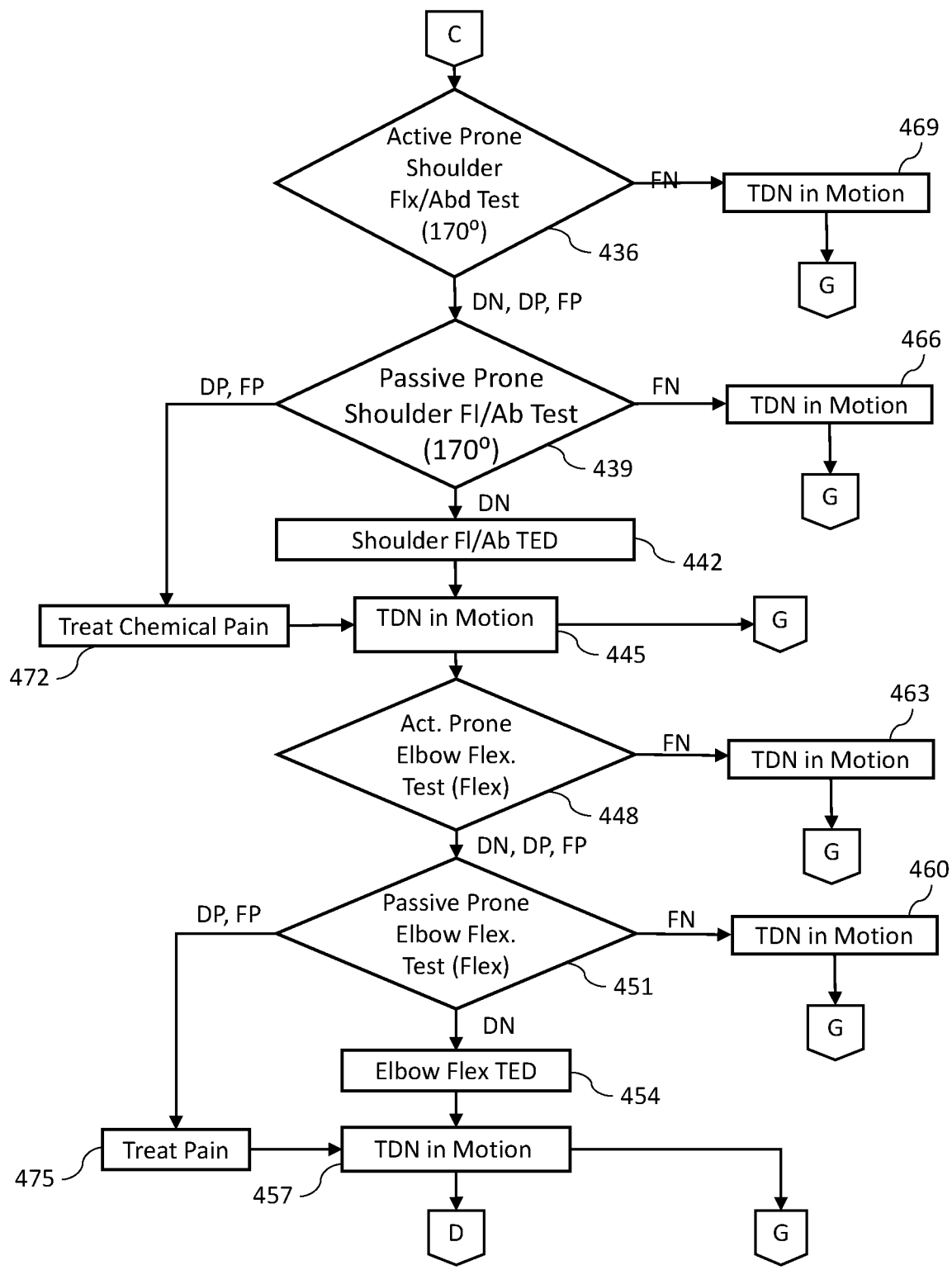
Figure 4B-Limited Upper Extremity Pattern 2

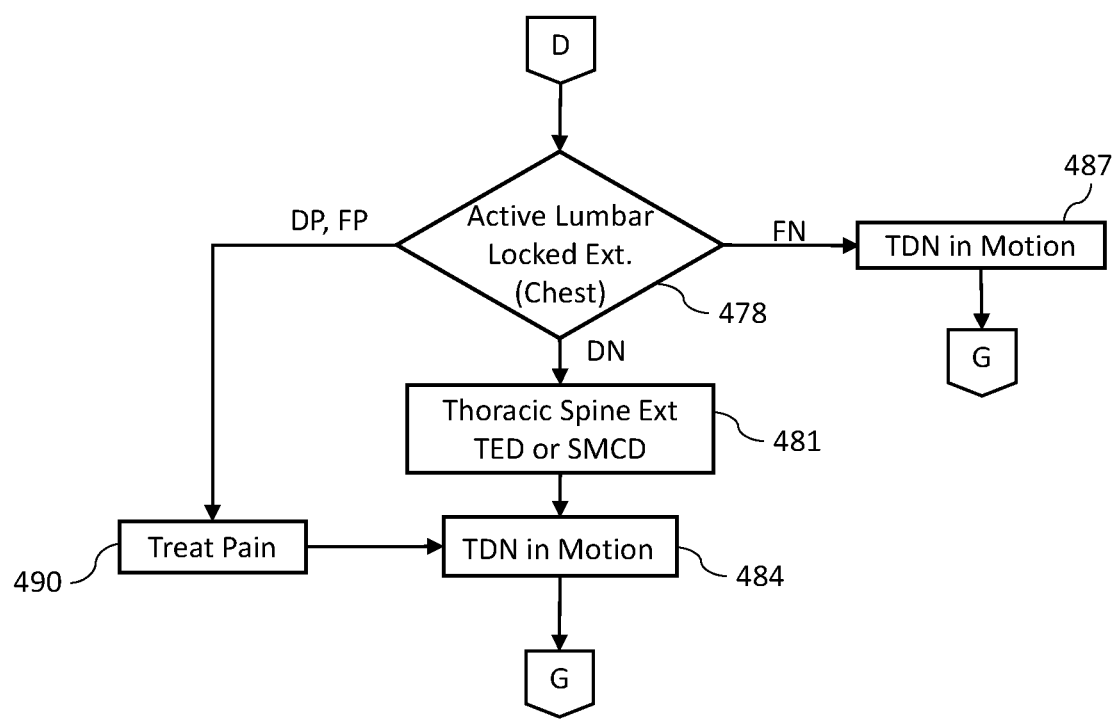
Figure 4C-Limited Upper Extremity Pattern 2

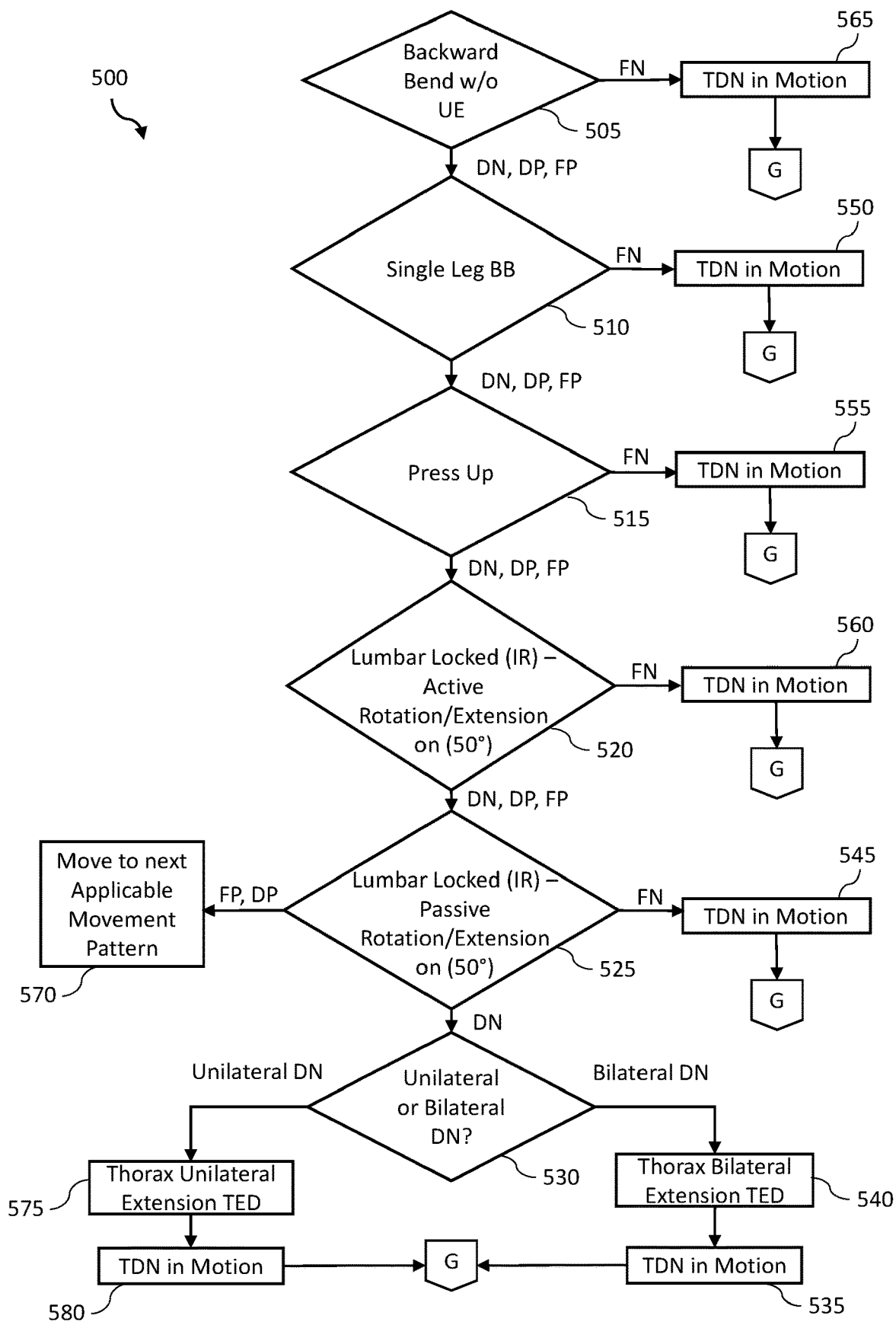
Figure 5-Spine Extension

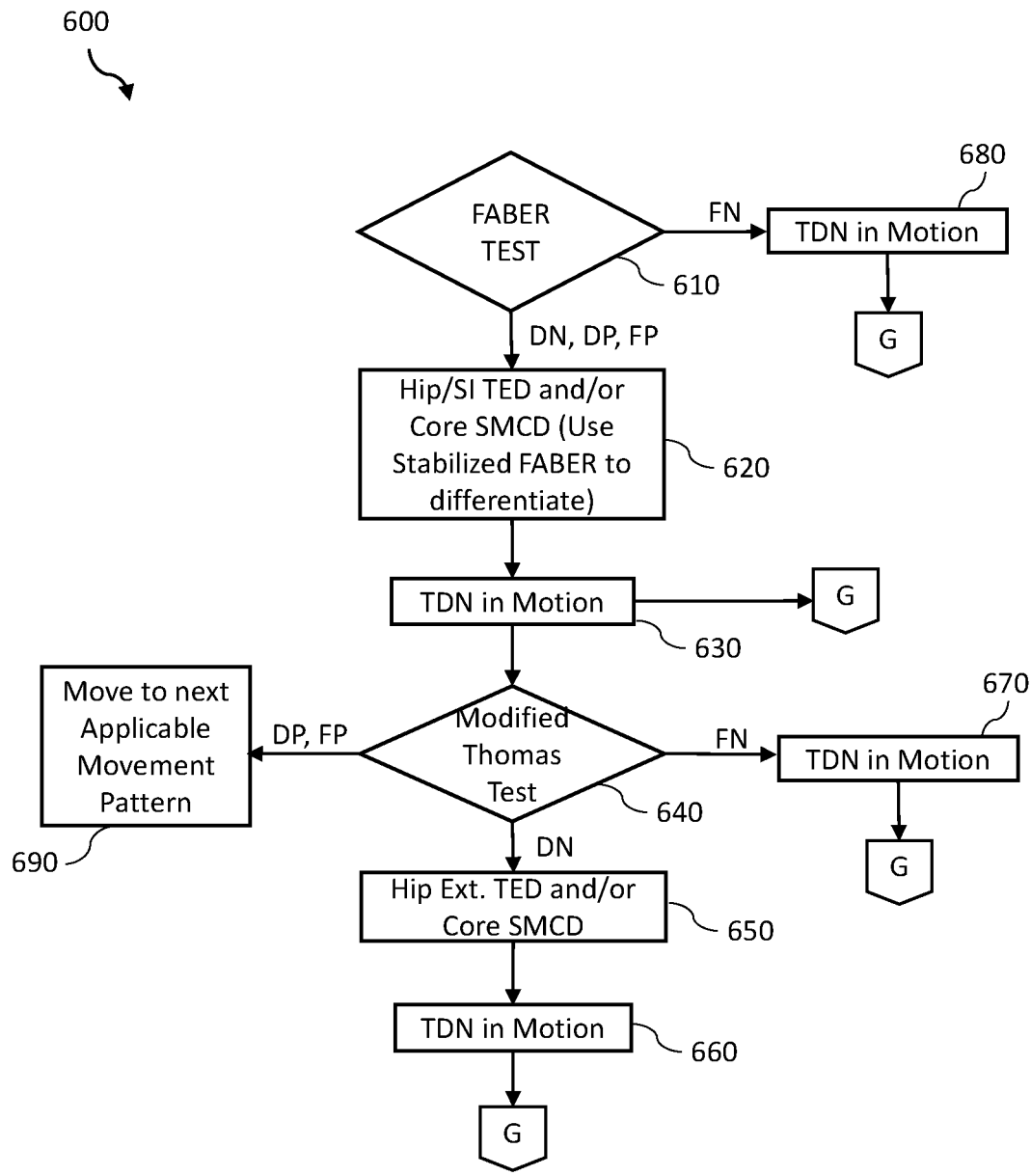
Figure 6-Lower Body Extension

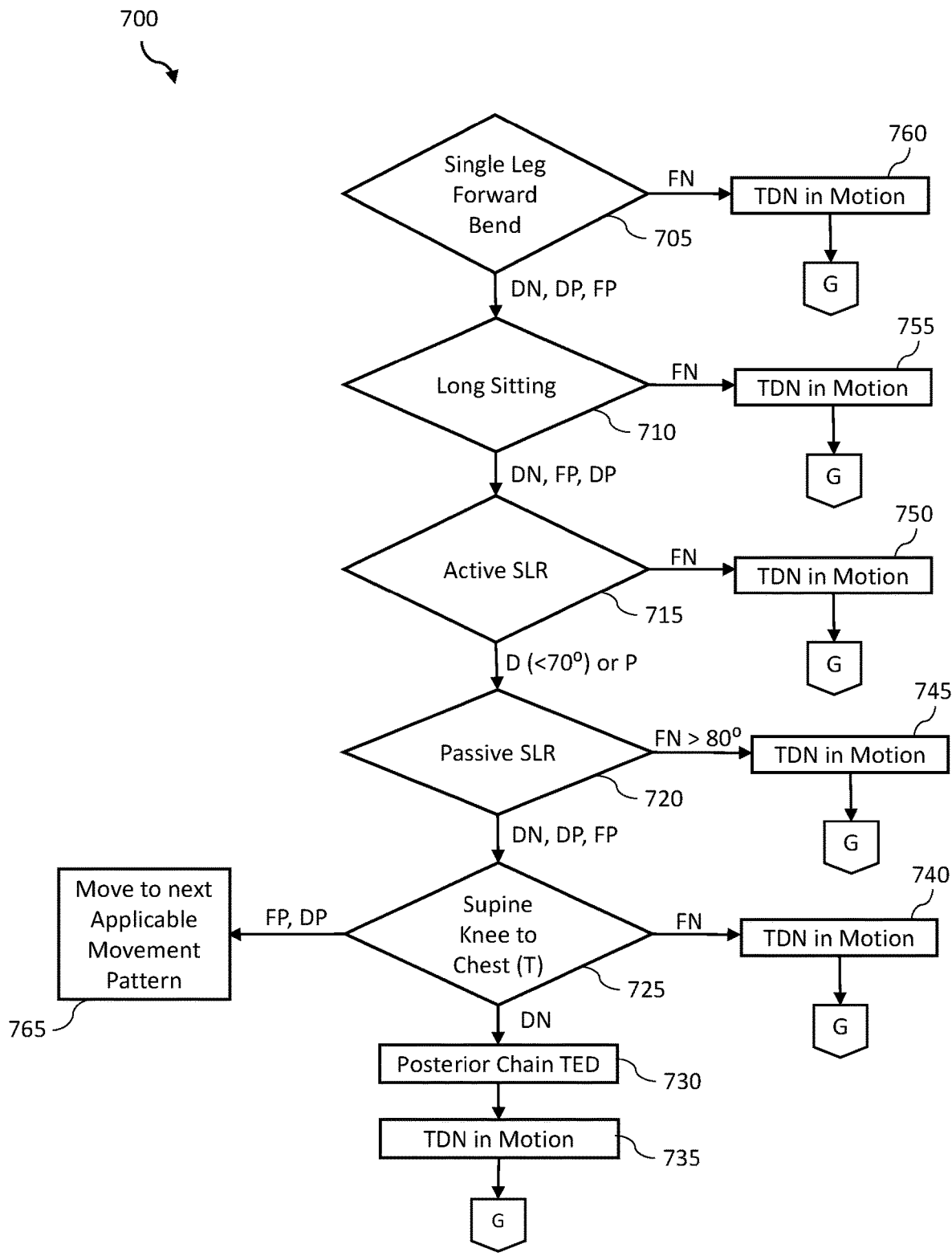
Figure 7-Limited Multi-Segmental Flexion

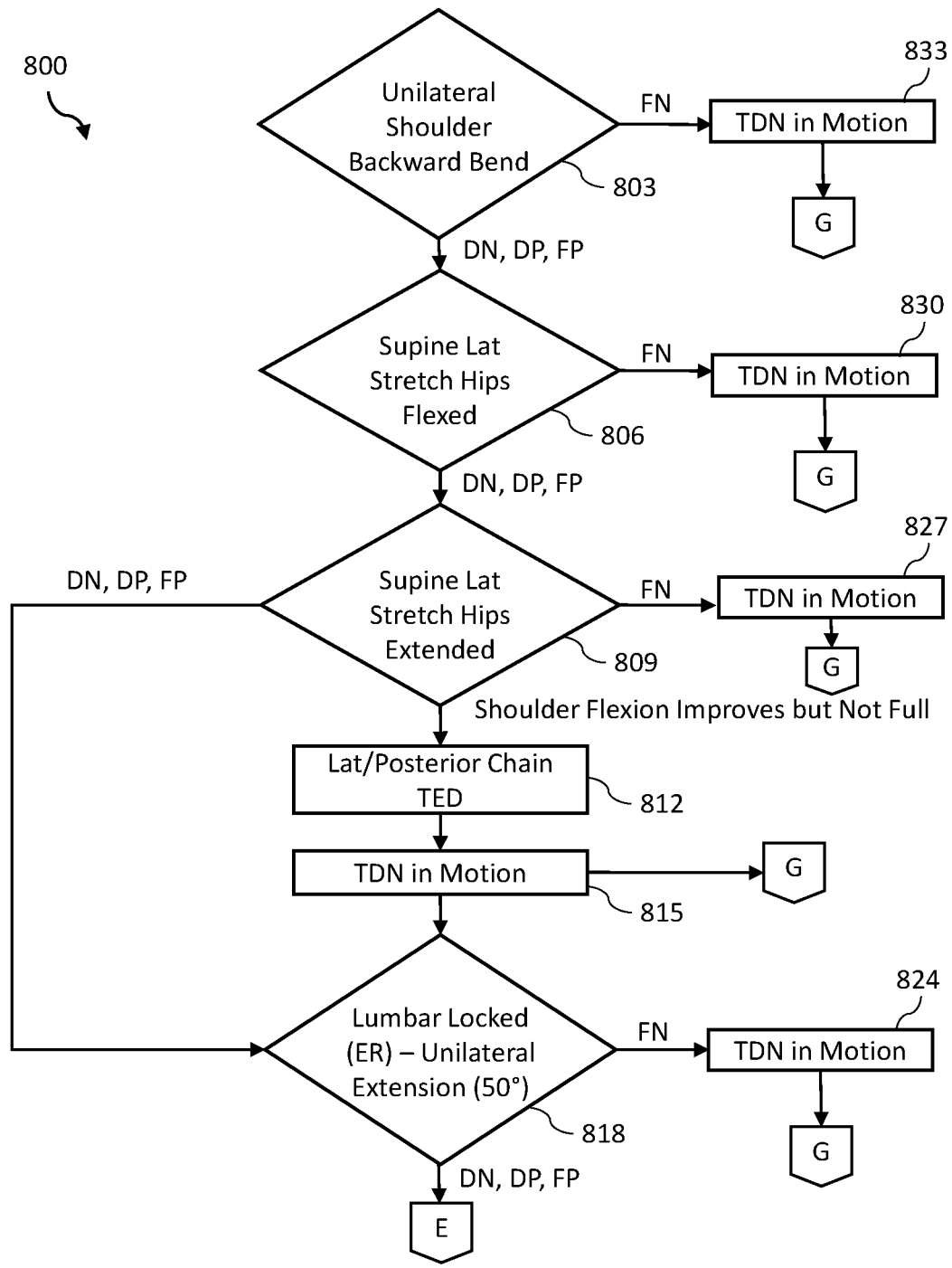
Figure 8A-Upper Body Extension

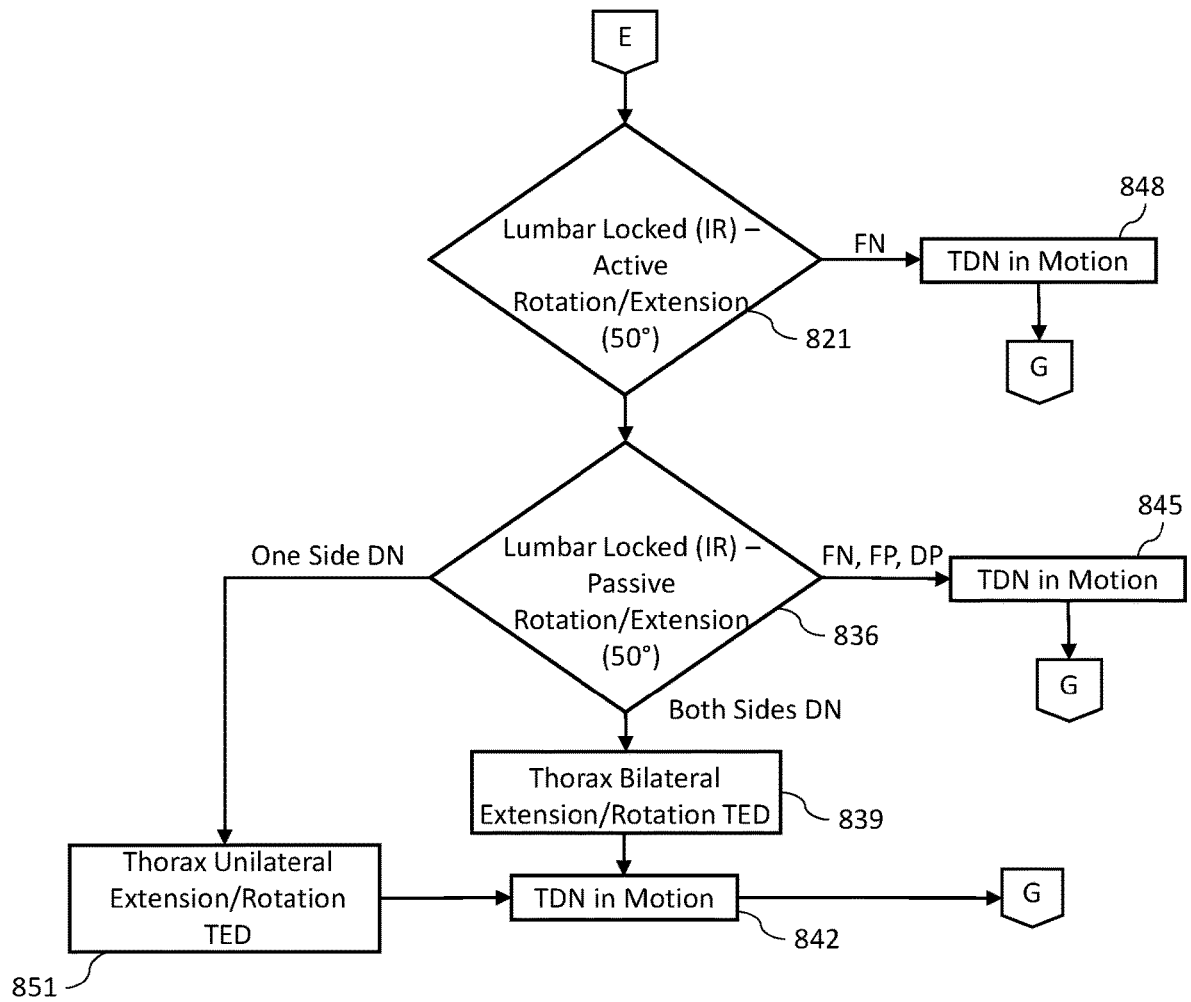
Figure 8B-Upper Body Extension

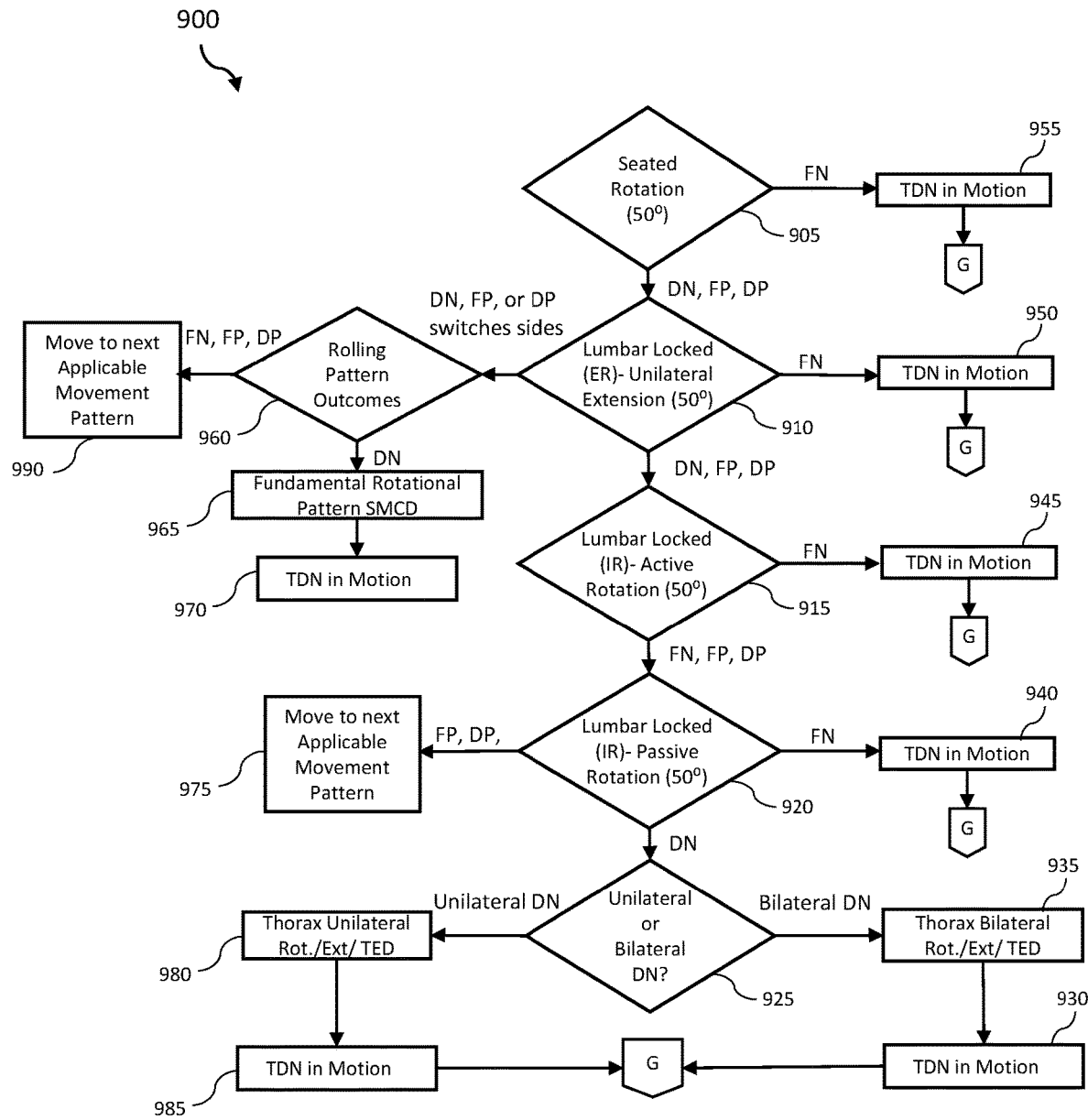
Figure 9- Limited Multi-Segmental Rotation

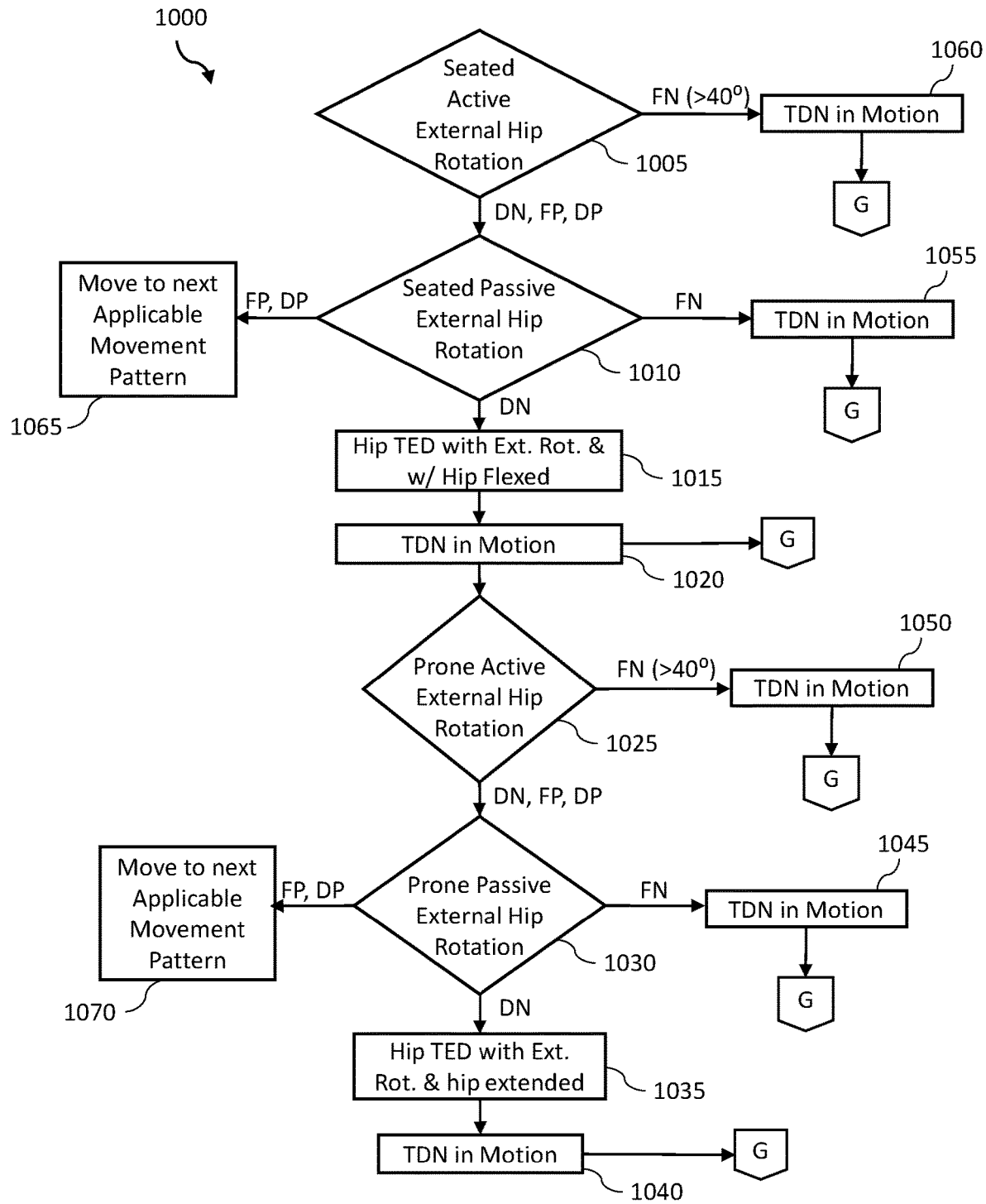
Figure 10- Hip Rotation Flow Chart
Part 1

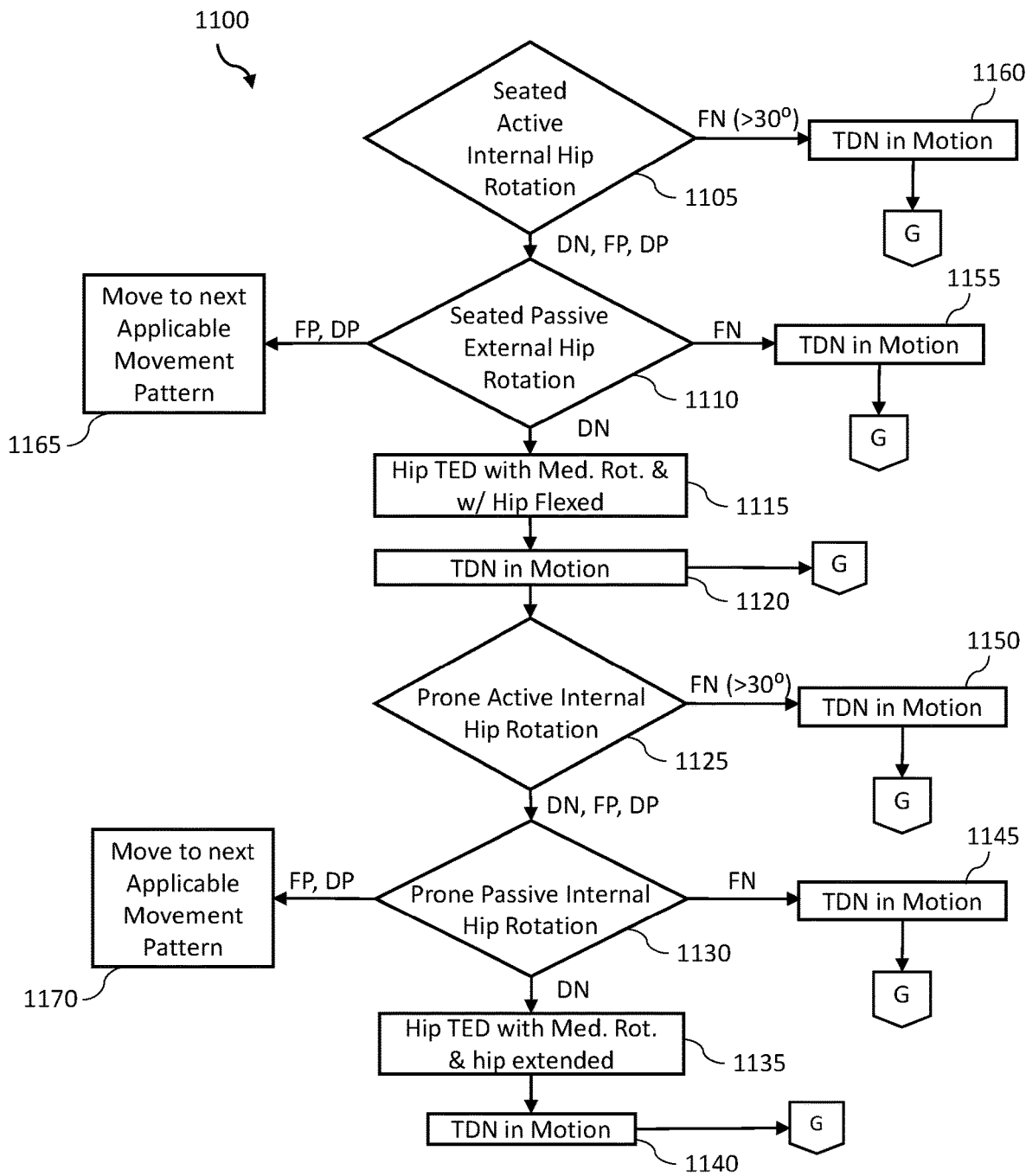
Figure 11- Hip Rotation Flow Chart
Part 2

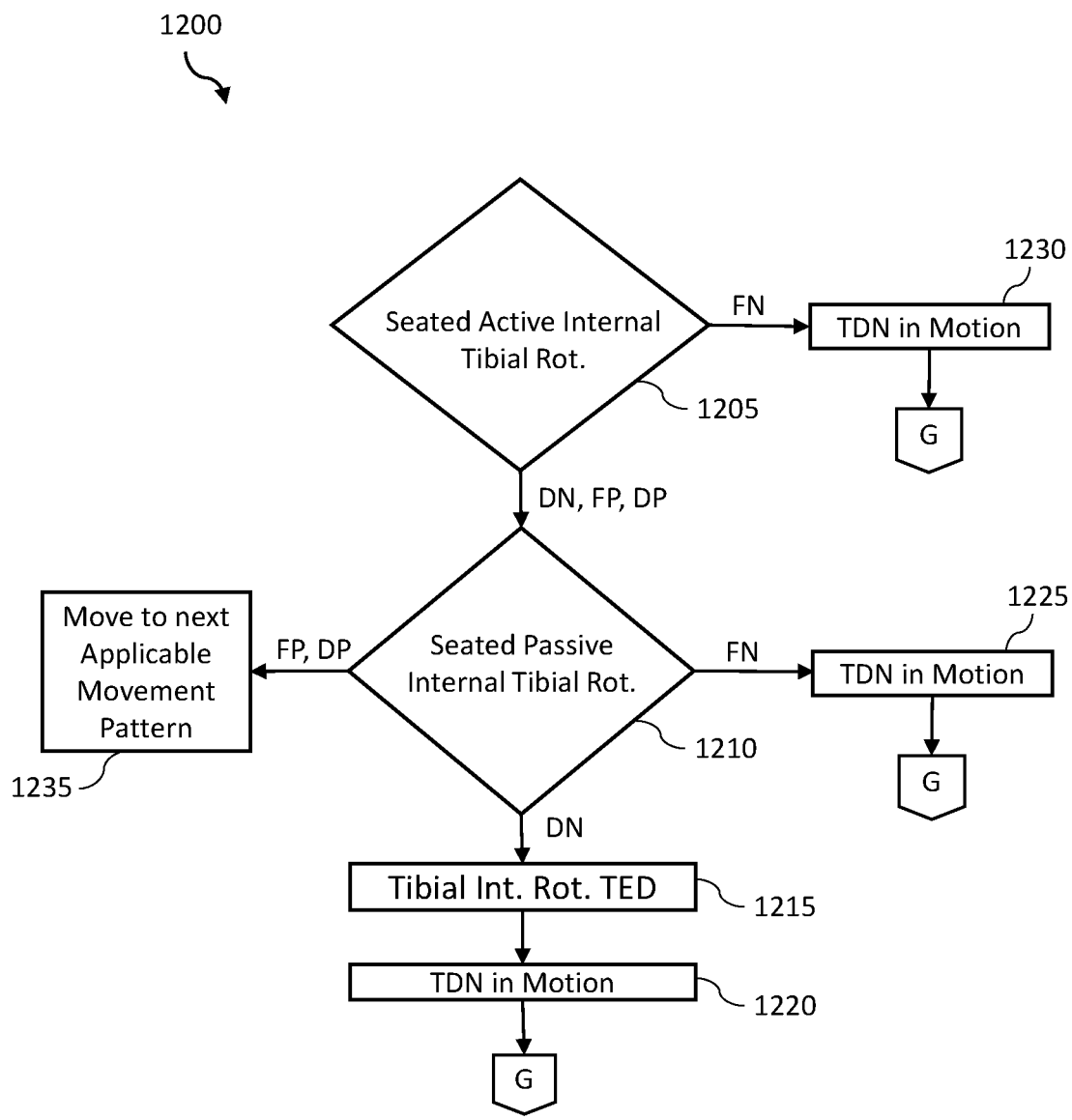
Figure 12A- Tibial Rotation

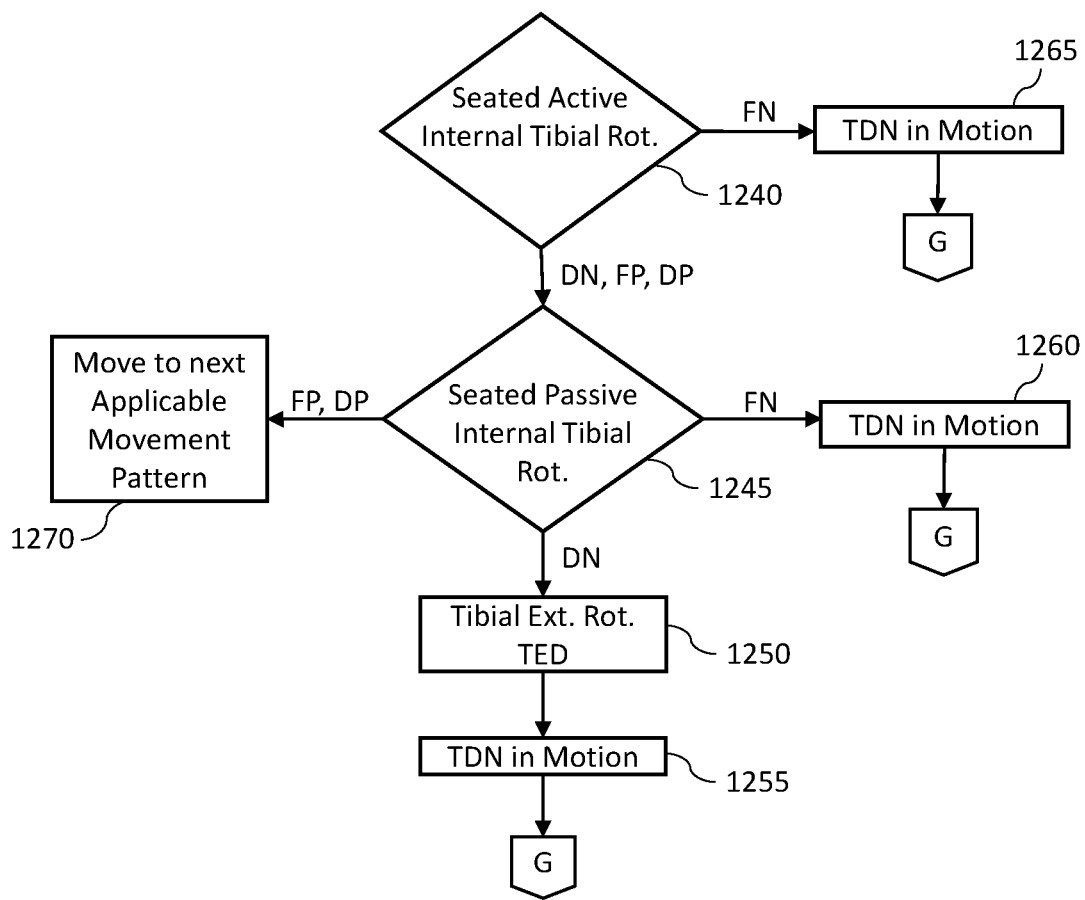
Figure 12B- Tibial Rotation

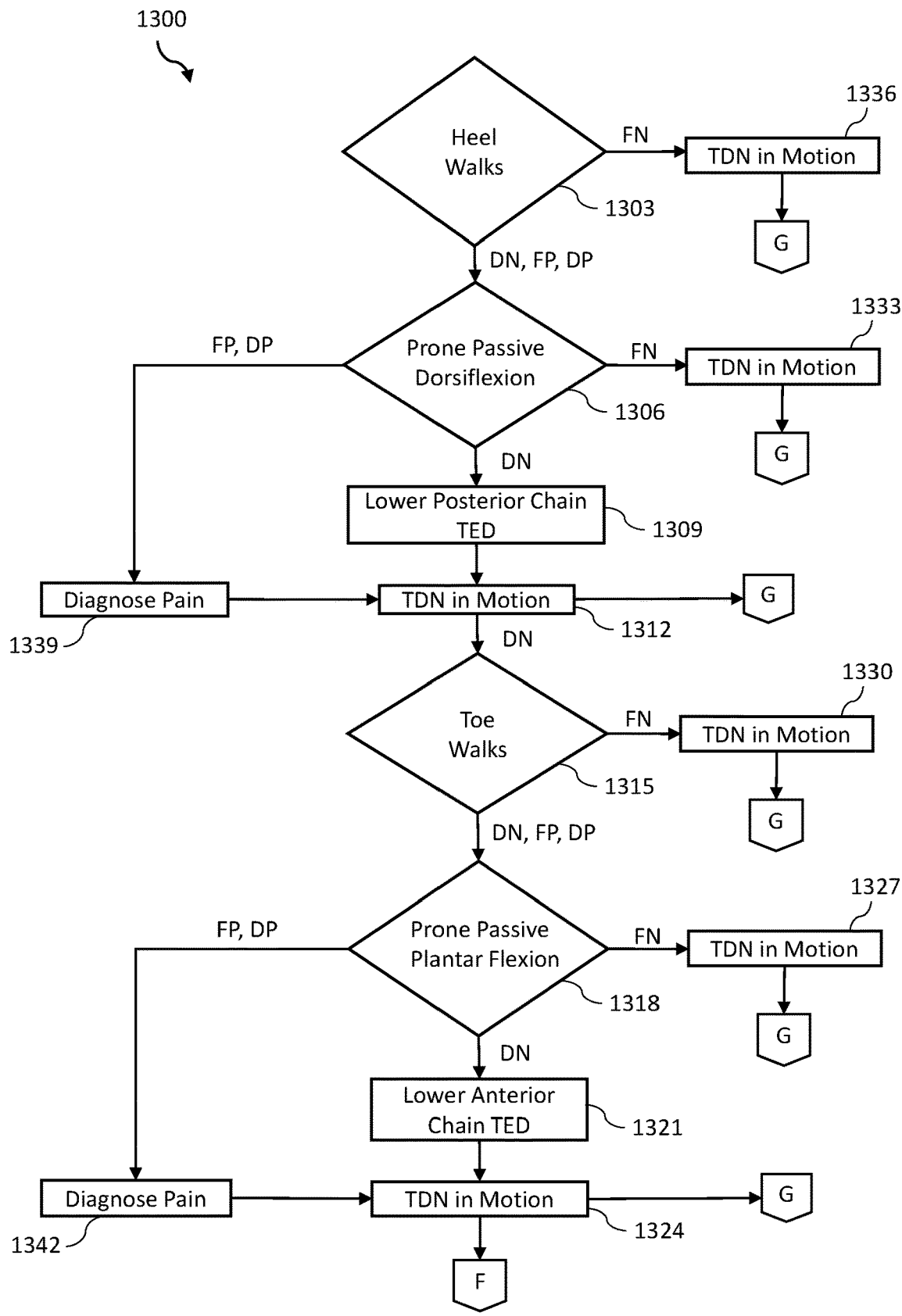
Figure 13A - Ankle Flowchart

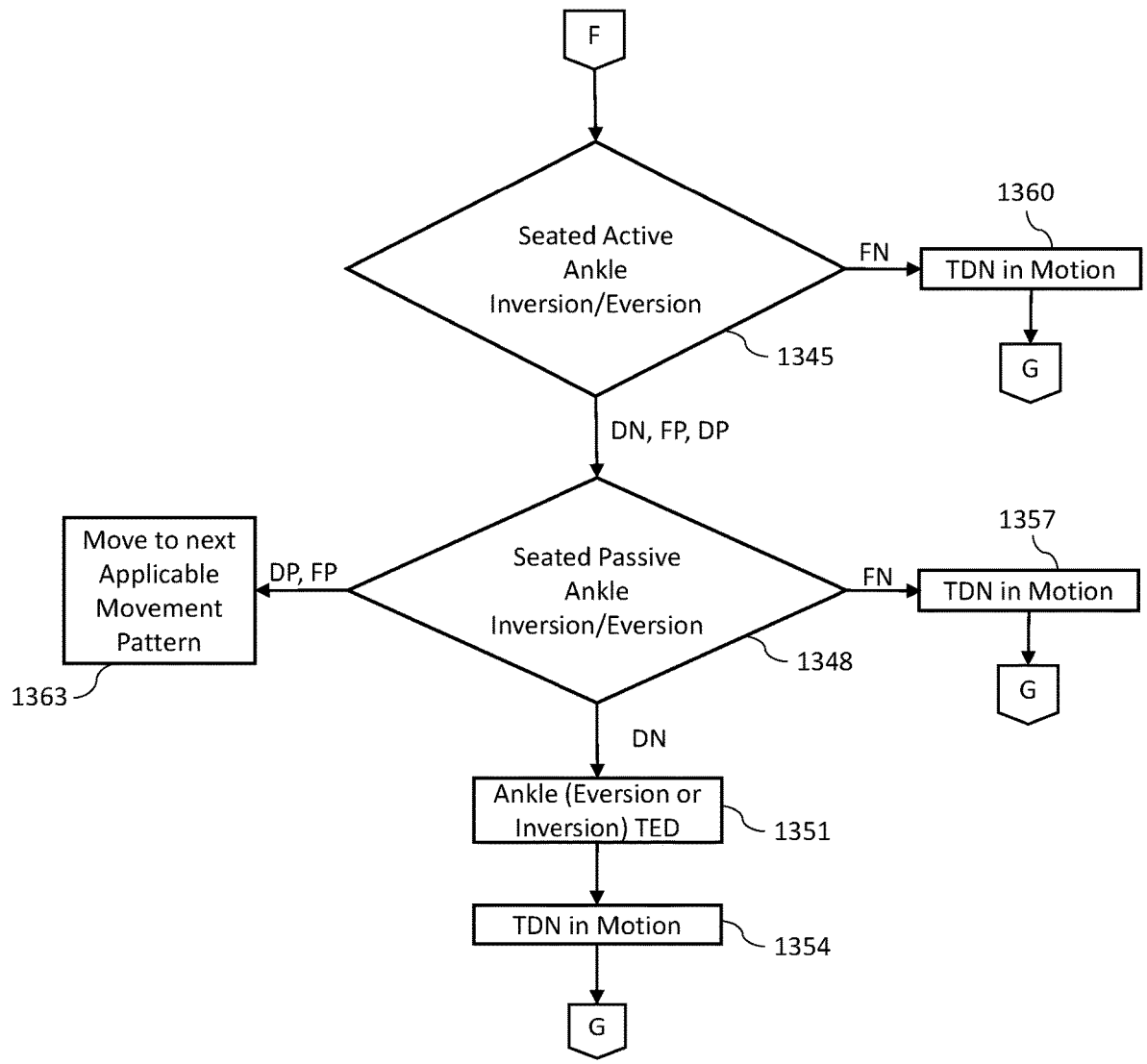
Figure 13B - Ankle Flowchart

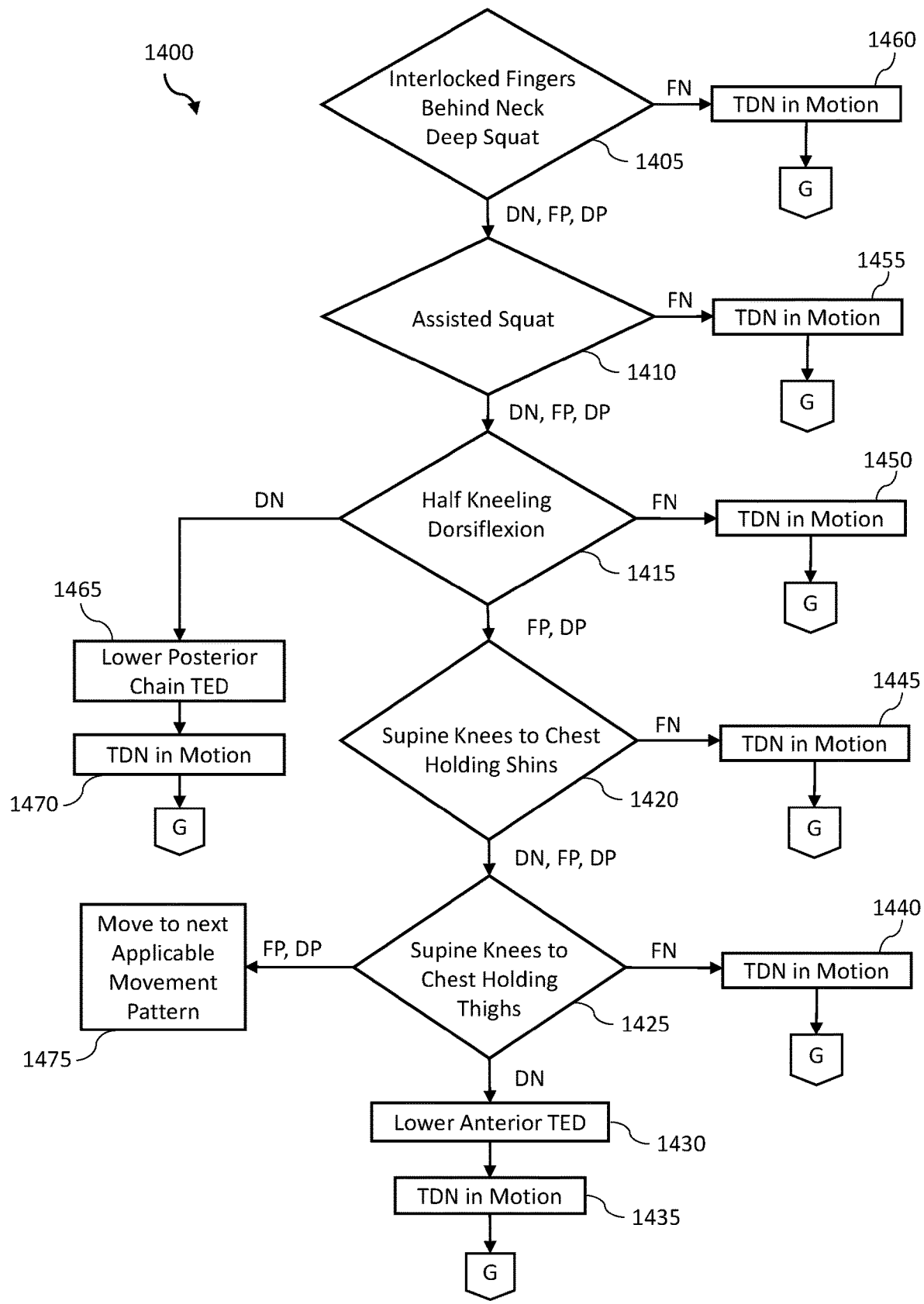
Figure 14 - Limited Overhead Deep Squat

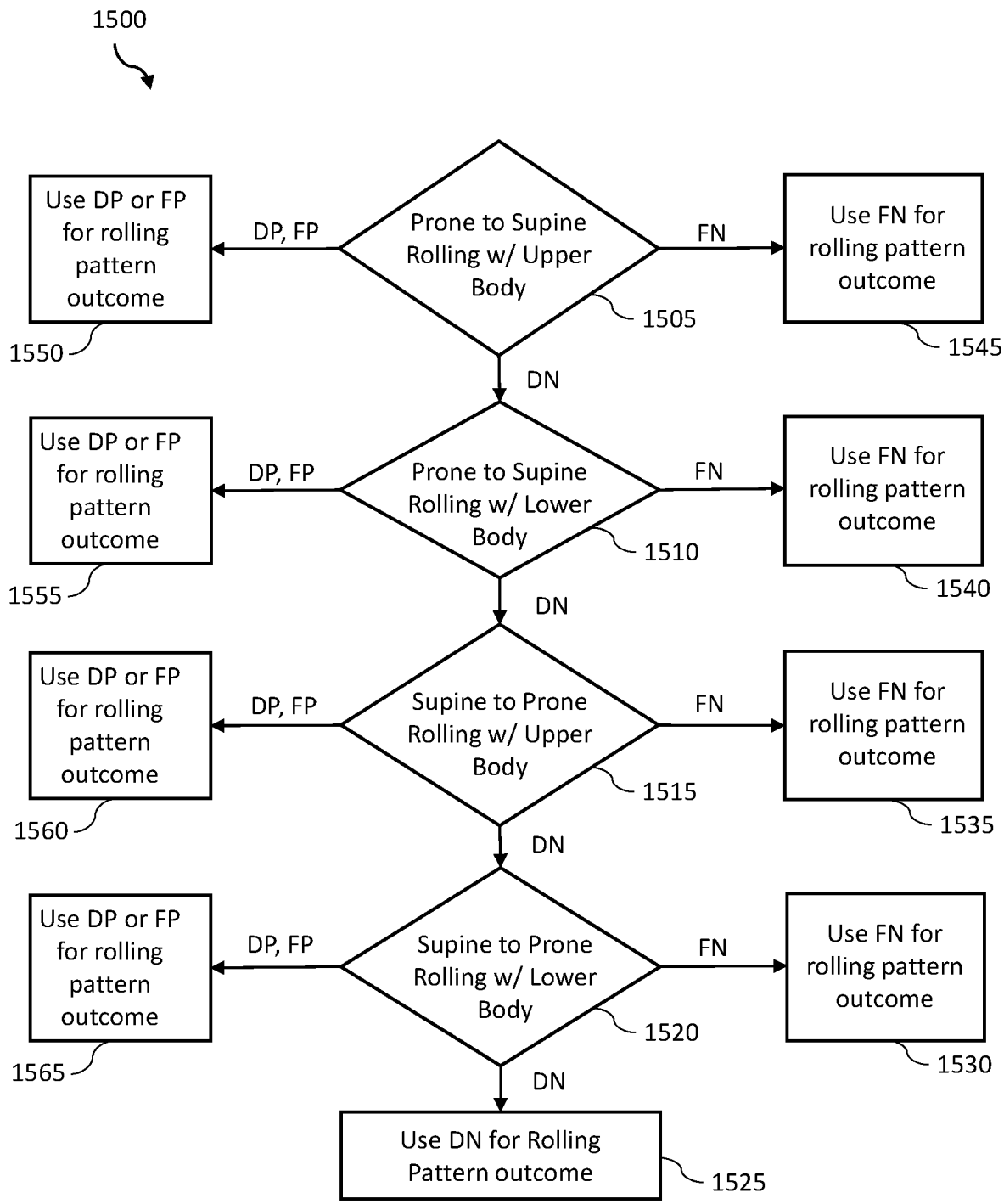
Figure 15 - Rolling

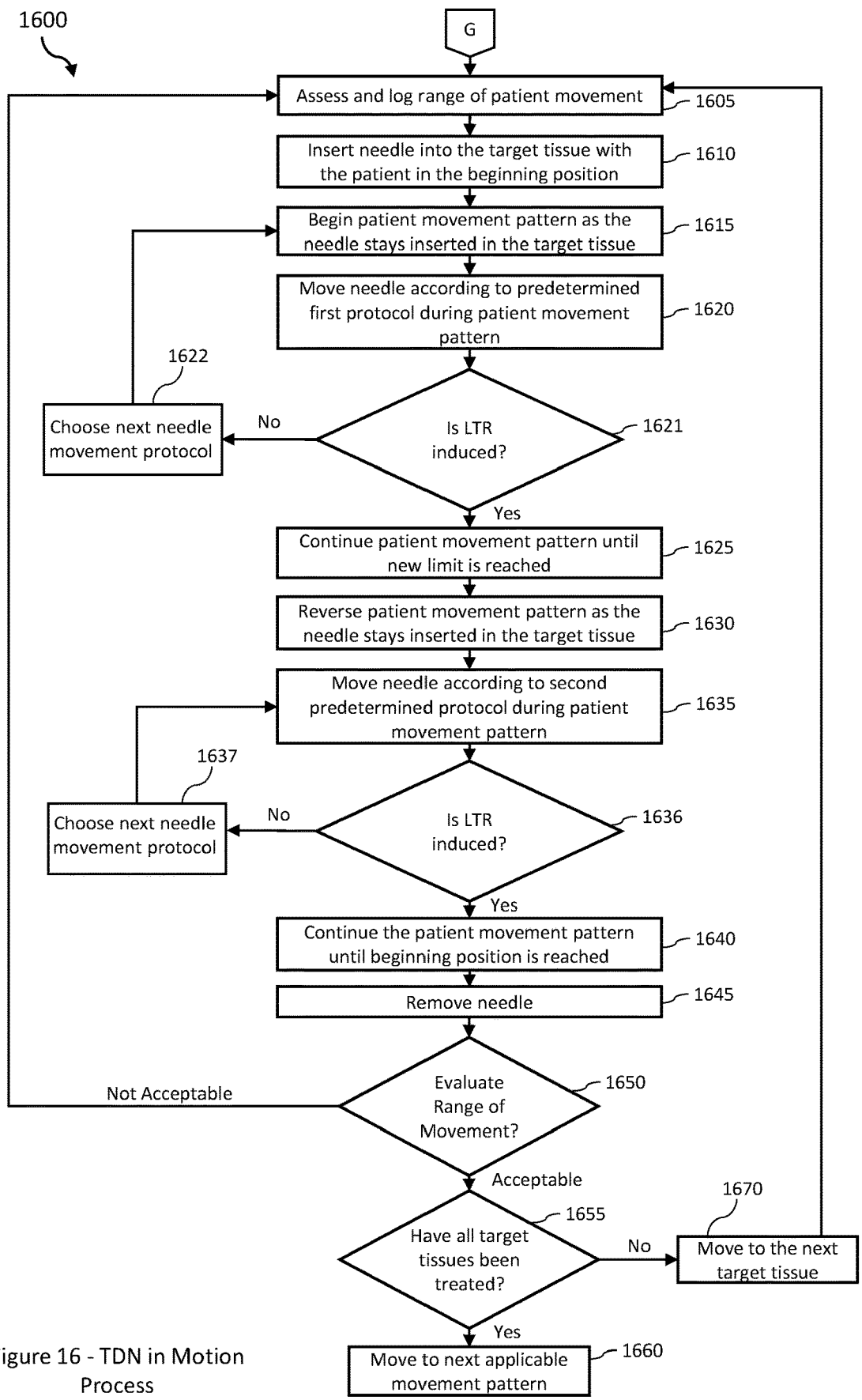
Figure 16 - TDN in Motion Process

| Amplitude (mm) | Frequency (movements/s) |
|---|---|
| 1 | 3.00 |
| 2 | 2.72 |
| 3 | 2.44 |
| 4 | 2.17 |
| 5 | 1.89 |
| 6 | 1.61 |
| 7 | 1.33 |
| 8 | 1.06 |
| 9 | 0.78 |
| 10 | 0.50 |
Figure 18A- Predefined Amplitude and Frequencies for Vertical Needle Protocol

| Amplitude (mm) | Frequency (movements/s) |
|---|---|
| 1 | 2.50 |
| 2 | 2.38 |
| 3 | 2.26 |
| 4 | 2.14 |
| 5 | 2.03 |
| 6 | 1.91 |
| 7 | 1.79 |
| 8 | 1.67 |
| 9 | 1.55 |
| 10 | 1.43 |
| 11 | 1.32 |
| 12 | 1.20 |
| 13 | 1.08 |
| 14 | 0.96 |
| 15 | 0.84 |
| 16 | 0.72 |
| 17 | 0.61 |
| 18 | 0.49 |
| 19 | 0.37 |
| 20 | 0.25 |
Figure 18B - Predefined Amplitude and Frequencies for Fanning Needle Protocol

Figure 18C- Predefined Amplitude and Frequencies for Rotational Needle Protocol

| DEPTH FROM SKIN SURFACE | DIAMETER |
|---|---|
| 1/4" – 1/2" | .12mm |
| 1/2" – 3/4" | .14mm |
| 3/4" – 1" | .16mm |
| 1" – 1/4" | .18mm |
| 1 ¼" – 1 ½" | .20mm |
| 1 ½" – 1 ¾" | .25mm |
| 1 ¾" – 2" | .30mm |
| 2" – 2 ¼" | .35mm |
| 2 ¼" and up | .40mm |

Figure 20 - TDN Needle Sizing Chart

TRIGGER POINT DRY NEEDLING IN MOTION AND METHOD OF USE

FIELD OF THE DISCLOSURE

The present disclosure relates generally to a method of treating myofascial trigger points using Trigger Point Dry Needling ("TDN"). In particular, the present disclosure relates to a TDN method that requires needle insertion during a patient movement pattern.

BACKGROUND OF THE DISCLOSURE

Acute trauma and repetitive muscle use can cause damage to muscular tissues resulting in inflammation and prolonged contraction. The combination of inflammation and contraction results in a restriction of microcirculation. The restriction lowers the amount of oxygenated blood flow to the site and removal of waste. As a result, the site may become hypoxic from the lack of oxygen, resulting in formation of scar tissue around the injured muscles and connective tissue. Over time, such scar tissue often forms a myofascial trigger point. If not treated properly, myofascial trigger points can limit muscle function, causing compression and irritation of nerves with resulting biomechanical disturbances in gait and function. The disturbances manifest themselves in a symptomatic decrease range of motion and pain.

There are a numerous known techniques used to improve the range of motion and reduce the pain associated with a trigger point. TDN is one of the techniques used to treat myofascial trigger points that are not manually palpable. During TDN, a thin filiform needle is inserted directly into the myofascial trigger point. Insertion of the needle results in a stimulation of the underlying muscle and tissue. The stimulation in many cases releases and inactivates the myofascial trigger point. This stimulation is also known to cause what is known as a Local Twitch Response ("LTR"). The LTR is an involuntary spinal cord reflex that causes a muscle to visibly contract. It can be diagnosed immediately through tactile feedback through a filiform needle. An LTR is critically valuable to the TDN process because it allows recognition of the existence and location of a myofascial trigger point. However, it is often times difficult to achieve an LTR without repeated needle use, which can cause unnecessary pain and muscle damage.

In the prior art, TDN is typically performed with the patient fixed and relaxed position and with no movement of the patient whatsoever during treatment. It is thought that motionless application of TDN prevents or lessens muscle damage during treatment.

The prior art discloses various methods of acupuncture intended to improve a muscle's range of motion and relieve pain, but none are directed at targeting myofascial trigger points using TDN and none require inserting needles at specific angles and specific needle movement protocols as a patient executes a specific repetitive body motion in order to induce LTR.

For example, U.S. Patent Publication No. 2014/0128899 to Shin discloses a method of treatment combining a motion style treatment with acupuncture. The method includes applying a "chuna" treatment to relax injured muscles or ligaments, then applying needles to acupuncture points while a patient slowly walks with the help of assistants. Once the patient walks without pain, treatment is terminated. The needles are not manipulated during the procedure. Trigger points are not targeted.

U.S. Patent Publication No. 2006/0095087 to Shin discloses a method of treatment of stiff muscles, ligaments, and nerves that combines a motion style treatment with acupuncture. The treatment comprises using "tui na" therapy to relax muscles. During treatment an acupuncture needle is inserted into a muscle at an "acupoint." The muscle is then moved to maximize circulation of "qi." The acupoints are not myofascial trigger points, but rather said to correspond to nerve pathways in the body.

U.S. Pat. No. 6,022,368 to Gavronsky discloses an apparatus for treatment using acupuncture. The apparatus consists of a convex enclosure that includes an acupuncture needle. The enclosure is sealed with adhesive tape. In use, the needle is inserted into the patient at the acupuncture site by puncturing the tape. Then, as the patient performs movement, if the patient does not feel an acupuncture sensation from the needle, a downward pressure is applied to the needle by flattening the enclosure.

It has been recognized by the inventor that TDN is rarely successful unless an LTR is induced. Hence, there is a need for a TDN method to ensure that an LTR will be induced to treat myofascial trigger points that does not require excessive treatment. There is also a need for a TDN method that combines modern patient movement patterns with planned and controlled needle movement protocols at a myofascial trigger point to optimize TDN treatment to maximize therapeutic effect.

SUMMARY OF THE DISCLOSURE

After evaluation of a sequence of patient movement patterns, if a painful, limited, or dysfunctional movement pattern is diagnosed to be cause by a myofascial trigger point, then the trigger point is treated using a combination of patient movement patterns and needle movement protocols to illicit an LTR response and effect treatment.

A sequence of movement patterns are performed in order to diagnose the reason a movement pattern is limited, painful, and/or dysfunctional, and then to identify a target tissue. Each movement pattern executed is evaluated using a score selected from functional painful ("FP"), functional non painful ("FN"), dysfunctional painful ("DP"), or dysfunctional non painful ("DN"). If any movement pattern is evaluated FN, then no further inquiry is required and the process moves to the next movement pattern to test. If a sequence results in a movement pattern diagnosed as Stability/Motor Control Dysfunction ("SMCD"), Tissue Extensibility Dysfunction ("TED"), then the movement pattern is treated using a preferred embodiment of the TDN method.

In a preferred embodiment of the TDN method, an assessment of range of movement of a particular movement pattern is made. After assessment, a needle is inserted into the target tissue at the location of the myofascial trigger point. As the patient performs a movement pattern, the needle is moved following a first needle movement protocol until a new maximum movement range is reached. Patient movement is then reversed and the needle is moved following a second needle movement protocol until the beginning position of the movement pattern is reached. If no LTR is induced then the needle movement protocol is changed according to a controlled schedule to effect maximum treatment efficiency and minimum muscle damage. Once the patient achieves an acceptable range of motion, the next specified movement pattern is assessed and the technique is performed again while motion range is monitored. The process is continued until all movement pattern sequences have been evaluated and all target tissues have been treated.

Those skilled in the art will appreciate the above-mentioned features and advantages of the disclosure together with other important aspects upon reading the detailed description that follows in conjunction with the drawings.

BRIEF DESCRIPTION OF THE DRAWINGS

FIG. 2A is a flowchart of the steps involved in diagnosing cervical spine flexion pain or dysfunction.

FIG. 2B is a flowchart of the steps involved in diagnosing cervical spine rotation pain or dysfunction.

FIG. 2C is a flowchart of the steps involved in diagnosing cervical spine extension pain or dysfunction.

FIGS. 3A-3C are a flowchart of the steps involved in diagnosing upper extremity internal rotation pain or dysfunction.

FIGS. 4A-4C are a flowchart of the steps involved in diagnosing upper extremity external rotation pain or dysfunction.

FIG. 5 is a flowchart of the steps involved in diagnosing spine extension pain or dysfunction.

FIG. 6 is a flowchart of the steps involved in diagnosing lower body extension pain or dysfunction.

FIG. 7 is a flowchart of the steps involved in diagnosing limited multi-segmental flexion pain or dysfunction.

FIGS. 8A and 8B are a flowchart of the steps involved in diagnosing upper body extension pain or dysfunction.

FIG. 9 is a flowchart of the steps involved in diagnosing limited multi-segmental rotation pain or dysfunction.

FIG. 10 is a flowchart of the steps involved in diagnosing if external hip rotation pain or dysfunction.

FIG. 11 is a flowchart of the steps involved in diagnosing internal hip rotation pain or dysfunction.

FIG. 12A is a flowchart of the steps involved in diagnosing internal tibial rotation pain or dysfunction.

FIG. 12B is a flowchart of the steps involved in diagnosing external tibial rotation pain or dysfunction.

FIGS. 13A and 13B are flowcharts of the steps involved in diagnosing ankle movement pain or dysfunction.

FIG. 14 is a flowchart of the steps involved in diagnosing overhead deep squatting pain or dysfunction.

FIG. 15 is a flowchart of the steps involved in determining a Rolling Pattern Outcome Scores.

FIG. 16 is a flowchart of the steps of a preferred embodiment of the TDN method.

FIG. 18A is a table of predefined amplitudes and frequencies for a preferred embodiment of a needle movement protocol.

FIG. 18B is a table of predefined amplitudes and frequencies for a preferred embodiment of a needle movement protocol.

FIG. 18C is a table of predefined amplitude and frequencies for a preferred embodiment of a rotational needle protocol.

FIG. 20 is a table showing different needle sizes used during various preferred embodiments of the TDN method.

DETAILED DESCRIPTION

Figure 1A:
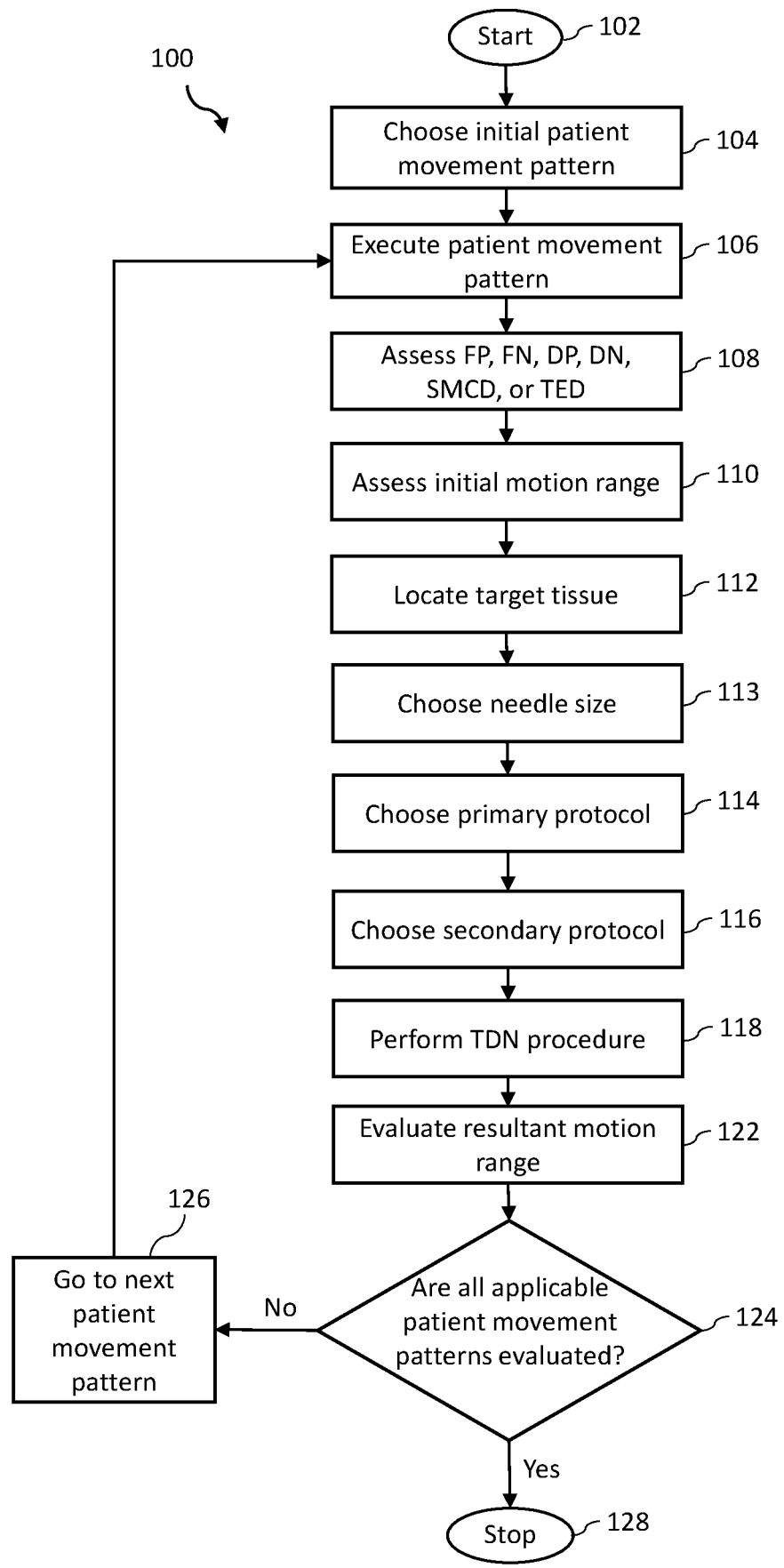
FIG. 1A is a flow chart of a preferred embodiment of the TDN motion method.

Referring then to FIG. 1A, flow chart 100 is shown and describes a preferred embodiment of the TDN motion method. The method begins at step 102. At step 104, an initial patient movement pattern is chosen, as will be further described. In a preferred embodiment of the TDN motion method, those movement patterns described in FIG. 2A-FIG. 15 are used. Other movement patterns may be employed to supplement those movement patterns described in this disclosure.

Each patient movement pattern includes a beginning position, a forward movement pattern, an ending position, and a reverse movement pattern. A patient starts at the beginning position. The forward movement pattern transitions the parts of the body from the beginning position to the ending position. The reverse movement pattern transitions back from the ending position back to the beginning position. The ending position is the point where the forward movement pattern is limited and stopped based on a physical limit of the body or a limit of the pain threshold of the patient. The ending position may change during treatment.

At step 106, the patient is positioned and executes the chosen patient movement pattern. The patient is instructed to perform the forward movement pattern from the beginning position until the point where the forward movement pattern is limited either physically by joint of the body or by a pain threshold of the patient, which defines the ending position.

At step 108, FP, FN, DP, DN, SMCD, and TED are evaluated. At step 110, initial motion range of the patient is assessed. At step 112, target tissue is located. In a preferred embodiment, the target tissue is the myofascial trigger point. In this step, muscle fiber direction, muscle fiber location, muscle size, needle entry axis, trigger point size, trigger point location and depth from the skin surface, and potential for LTR are evaluated.

At step 113, needle size is chosen based on the depth of the trigger point from the skin surface. In a preferred embodiment, the diameter of the needle is chosen according to the table shown in FIG. 19. In another preferred embodiment, the brand of needle chosen is a Myotech™ Dry Needle supplied by Red Coral® located in Melbourne, Australia. In another preferred embodiment, the needle is encased in a protective holder, which allows exact manipulation and control of entry angle, such as shown in U.S. Pat. No. 6,808,499, the disclosure of which is incorporated herein by reference. At step 114, a primary needle movement protocol is selected. The primary needle movement protocol, amplitude and frequency, are chosen in this step. At step 116, a secondary protocol is chosen. A frequency and amplitude for the secondary protocol is also chosen at this step. In a preferred embodiment, a single needle movement protocol is employed. At step 118, the TDN motion procedure is performed. In one preferred embodiment, the TDN motion procedure of FIG. 16 is performed at this step. At step 122, resultant patient motion of range is evaluated for acceptability. At step 124, a decision is made as to whether or not all patient movement patterns have been evaluated. If not, then at step 126, the next patient movement pattern is chosen and the method returns to step 106. If so, then the method moves to step 128 and concludes.

Figure 1B:
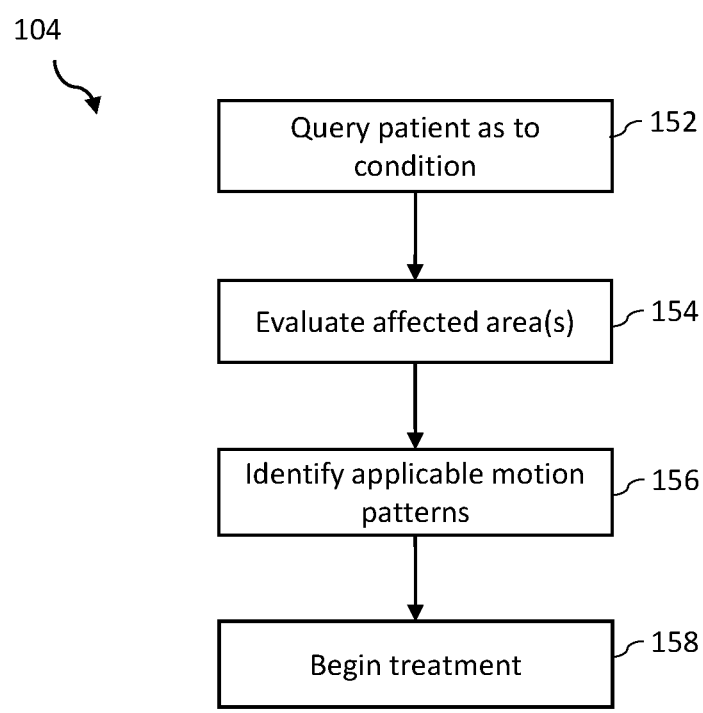
FIG. 1B is a flow chart of a preferred embodiment of a method of choosing an initial patient movement pattern.

Referring then to FIG. 1B, flow chart 104 is shown and describes a preferred embodiment of the step 104 of FIG. 1A. At step 152, the patient is queried as to the location of pain, limited movement, or affected gate. At step 154, the affected areas are evaluated for the presence of myofascial trigger points and range of motion. At step 156, applicable motion patterns for treatment are identified and listed. This list is used as a subset of motion patterns, which are further evaluated for treatment. At step 158 treatment starts.

FIG. 2A is a flowchart 200 representing the steps involved in diagnosing whether a cervical flexion movement pattern is painful, limited, or dysfunctional due to a myofascial trigger point, determining the target tissue to be treated, and determining the movement pattern to be used during treatment. At step 203, the patient executes the Active Supine Cervical Flexion Test and is evaluated. This test requires a patient to touch the chin to the sternum in the supine position. If a score of FN is given at step 203, then at step 224, the process moves to the TDN in motion process. If a score of DN, DP, or FP is given at step 203, then the process continues to step 206.

At step 206, the patient executes the Passive Supine Cervical Flexion Test and is evaluated. This test requires the patient's cervical spine to be flexed in the same manner as the Active Supine Cervical Flexion Test. If a score of FN is given at step 206, then at step 221, the process moves to the TDN in motion process. If a score of DN, DP, or FP is given at step 206, then the process continues to step 209.

At step 209, the patient executes the Active Supine Occipitoatlantal ("OA") Cervical Flexion Test (20 degrees) and is evaluated. This test requires the patient's head to be actively rotated to the side as far as possible, and then requires the patient to perform a chin tuck in the supine position. If a score of FN is given at step 209, then at step 218, the process moves to the TDN in motion process. If a score of FP or DP is given at step 209, then at step 227, the process moves to the next applicable movement pattern. If a score of DN is given at step 209, then at step 212, the patient is diagnosed with OA Flexion TED, and is treated by applying the Active Supine OA Cervical Flexion Test (20 degrees) to the TDN in motion process at step 215, as shown in FIG. 16.

FIG. 2B is a flowchart representing the steps involved in diagnosing whether a supine cervical rotation pattern is painful, limited, or dysfunctional due to a myofascial trigger point, determining the target tissue to be treated, and determining the movement pattern to be used during treatment. At step 230, the patient executes the Active Supine OA Cervical Rotation Test (80 degrees) and is evaluated. This test requires the patient to rotate the head to the side as far as possible in the supine position with the arms and hands by the thighs. If a score of FN is given at step 230, then at step 251, the process moves to the TDN in motion process. If a score of DN, DP, or FP is given at step 230 the process continues to step 233.

At step 233, the patient executes the Passive Supine Cervical Rotation Test and is evaluated. This test requires the patients head to be rotated to the side in the same manner as the Active Supine Cervical Rotation Test. If a score of FN is given at step 233, then at step 248, the process moves to the TDN in motion process. If a score of DN, DP, or FP is given at step 233, then the process continues to step 236.

At step 236, the patient executes the C1-C2 Cervical Rotation Test and is evaluated. This test requires that the patient's cervical spine be flexed while the back of the patient's head rests in the therapist's abdomen while the patient is in the supine position. The patient's head is then rotated to the right and left. If a score of FN is given at step 236, then at step 245, the process moves to the TDN in motion process. If a score of DP or FP is given at step 236, then at step 254, the process moves to the next applicable movement pattern. If a score of DN is given at step 236, then the patient is diagnosed with C1-C2 TED at step 239, and is treated by applying the C1-C2 Cervical Rotation Test to the TDN in motion process at step 242, as shown in FIG. 16.

FIG. 2C is a flowchart representing the steps involved in diagnosing whether a supine cervical extension pattern is painful, limited, or dysfunctional due to a myofascial trigger point, determining the target tissue to be treated, and determining the movement pattern to be used during treatment. At step 257, the patient executes the Supine Cervical Extension Test and is evaluated. This test requires a patient to extend the neck downwards in an attempt to move the face perpendicular to the floor table, while the patient is in the supine position with the head hanging of the table. If a score of FN is given at step 257, then at step 266, the process moves to the TDN in motion process. If a score of DP or FP is given at step 257, then at step 269, the process moves to the next applicable movement pattern. If a score of DN is given at step 257, then at step 260, the patient is diagnosed with Cervical Extension TED, and is treated by applying the Supine Cervical Extension Test to the TDN in motion process at step 263, as shown in FIG. 16.

FIG. 3A-3C is flowchart 300 representing the steps involved in diagnosing whether an upper extremity internal rotation ("IR") movement pattern is painful, limited, or dysfunctional due to a myofascial trigger point, determining the target tissue to be treated, and determining the movement pattern to be used during treatment.

At step 303, the patient executes the Active Prone Upper Extremity Pattern One (IR) and is evaluated. This test requires the patient to attempt to touch the opposite inferior angle of the scapula by reaching up and behind the back in the prone position while keeping the other arm and hand resting by the thigh. If a score of FN is given at step 303, at step 330, the process moves to the TDN in motion process. If a score of DN, DP, or FP is given at step 303 the process continues to step 306.

At step 306, the patient executes the Passive Prone Upper Extremity Pattern One (IR) and is evaluated. This test requires the patient's arm to be moved in the same manner as Active Prone Upper Extremity Pattern One (IR). If a score of FN is given at step 306, then at step 327, the process moves to the TDN in motion process. If a score of DN, DP, or FP is given at step 306, the patient continues to step 309.

At step 309, the patient executes the Active Prone Shoulder 90/90 IR Test (60 degrees) and is evaluated. This test requires the patient to internally rotate the shoulder as far as possible in the prone position with the arm hanging off the table with 90 degrees of shoulder abduction and 90 degrees of elbow flexion. If a score of FN is given at step 309, then at step 324, the process moves to the TDN in motion process. If a score of DN, DP, or FP is given at step 309, then the process continues to step 312.

At step 312, the patient executes the Passive Prone Shoulder IR Test and is evaluated. This test requires the patient's shoulder to be rotated from the prone position in the same manner as the Active Prone Shoulder 90/90 IR Test. If a score of FN is given at step 312, then at step 321, the process moves to the TDN in motion process. If a score of DP or FP is given at step 312, then at step 333, the patient is diagnosed with chemical pain, and is treated by applying the Passive Prone Shoulder IR Test to the TDN in motion process at step 318, as shown in FIG. 16. If a score of DN is given at step 312, then at step 315, the patient is diagnosed with Shoulder IR TED, and is treated by applying the Passive Prone Shoulder IR Test to the TDN in motion process at step 318, as shown in FIG. 16. After the TDN in motion process in completed for step 318, the process continues to step 336.

At step 336, the patient executes the Active Prone Shoulder Extension ("Ext.") Test (50 degrees) and is evaluated. This test requires the patient to raise an arm upwards while keeping the palms facing inward from a prone position while keeping the arms fully extended. If a score of FN is given at step 336, then at step 369, the process moves to the TDN in motion process. If a score of DN, DP, or FP is given at step 336, then the process continues to step 339.

At step 339, the patient executes the Passive Shoulder Extension Test and is evaluated. This test requires that the patient's shoulder be flexed in the same manner as the Active Prone Shoulder Extension Test in the prone position. If a score of FN is given at step 339, then at step 366, the process moves to the TDN in motion process. If a score of DP or FP is given at step 339, then at step 372, the patient is diagnosed with chemical pain, and is treated by applying the Passive Shoulder Extension Test to the TDN in motion process at step 345, as shown in FIG. 16. If a score of DN is given at step 339, then at step 342, the patient is diagnosed with Shoulder Extension TED, and is treated by applying the Passive Shoulder Extension Test to the TDN in motion process at step 345, as shown in FIG. 16. After completion of TDN in motion for step 345, the process continues to step 348.

At step 348, the patient executes the Active Prone Elbow Flexion Test (shoulder extended). This test requires a patient to touch the thumb to the shoulder by bending the elbow in the prone position. If a score of FN is given at step 348, then at step 363, the process moves to the TDN in motion process. If a score of DN, DP, or FP is given at step 348, then the process continues to step 351.

At step 351, the patient executes the Passive Prone Elbow Flexion Test (shoulder extended) and is evaluated. This test requires the patient's elbows to be flexed in the same manner as the Active Prone Elbow Flexion Test. If a score of FN is given at step 351, then at step 360, the process moves to the TDN in motion process. If a score of DP or FP is given at step 351, then at step 375, the patient is diagnosed with chemical pain, and is treated by applying the Passive Prone Elbow Flexion Test (shoulder extended) to the TDN in motion process at step 357, as shown in FIG. 16. If a score of DN is given at step 351, then at step 354, the patient is diagnosed with Elbow Flex TED, and is treated by applying the Passive Prone Elbow Flexion Test (shoulder extended) to the TDN in motion process step 357, as shown in FIG. 16. After the TDN in motion process is completed for step 357, the process continues to step 378.

At step 378, the patient executes the Active Lumbar Locked Extension (Chest) movement pattern and is evaluated. This movement pattern requires a patient enter into a full prone rocking position, sitting on the calves with one forearm centered in front of the knees and the other arm behind the back. The patient rotates the shoulder of the forearm that is behind the back up and back as far as possible while maintaining the prone rocking position. If a score of FN is given at step 378, then at step 387, the process moves to the TDN in motion process. If a score of DP or FP is given at step 378, then at step 390, the patient is diagnosed with pain, and is treated by applying an Active Lumbar Locked Extension (Chest) to the TDN in motion process at step 384, as shown in FIG. 16. If a score of DN is given at step 378, then at step 381, the patient is diagnosed with Thoracic Spine Extension TED or SMCD, and is treated by applying an Active Lumbar Locked Extension (Chest) movement pattern to the TDN in motion process at step 384, as shown in FIG. 16.

FIGS. 4A-4C is flowchart 400 representing the steps involved in diagnosing whether an upper extremity external rotation ("ER") movement pattern is painful, limited, or dysfunctional due to a myofascial trigger point, determining the target tissue to be treated, and determining the movement pattern to be used during treatment.

At step 403, the patient executes the Active Prone Upper Extremity Pattern Two (ER) test. This test requires the patient to attempt to touch the opposite superior angle of the scapula by reaching over the shoulder in the prone position while keeping the other arm and hand resting by the thigh. If a score of FN is given at step 403, then at step 430, the process moves to the TDN in motion process. If a score of DN, DP, or FP is given at step 403, then the process continues to step 406.

At step 406, the patient executes the Passive Prone Upper Extremity Pattern Two (ER) and is evaluated. This test requires the patient's arm to be moved in the same manner as the Active Prone Upper Extremity Pattern Two (ER). If a score of FN is given at step 406, then at step 427, the process moves to the TDN in motion process. If a score of DN, DP, or FP is given at step 406, then the process continues to step 409.

At step 409, the patient executes the Active Prone Shoulder 90/90 ER Test and is evaluated. This test requires the patient to externally rotate the shoulder as far as possible in the prone position with the arm hanging off the table with 90 degrees of shoulder abduction and 90 degrees of elbow flexion. If a score of FN is given at step 409, then at step 424, the process moves to the TDN in motion process. If a score of DN, DP, or FP is given at step 409, then the process continues to step 412.

At step 412, the patient executes the Passive Prone Shoulder ER Test and is evaluated. This test requires the patient's shoulder to be externally rotated in the same manner as the Active Prone Should 90/90 ER Test. If a score of FN is given at step 412, then at step 421, the process moves to the TDN in motion process. If a score of DP or FP is given at step 412, then at step 433, the patient is diagnosed with pain, and is treated by applying the Passive Prone Shoulder ER Test to the TDN in motion process at step 418, as shown in FIG. 16. If a score of DN is given at step 412, then at step 415, the patient is diagnosed with Shoulder ER TED, and is treated by applying the Passive Prone Shoulder ER Test to the TDN in motion process at step 418, as shown in FIG. 16. After TDN in motion process is completed for step 418, the process continues to step 436.

At step 436, the patient executes the Active Prone Shoulder Flexion/Abduction Test (170 degrees). This test requires the patient to lift an arm in both a forward direction parallel to the body and a direction perpendicular to the body while keeping the palms facing down and the arm fully extended in the prone position. If a score of FN is given at step 436, then at step 469, the process moves to the TDN in motion process. If a score of DN, DP, or FP is given at step 436, then the process continues to step 439.

At step 439, the patient executes the Passive Prone Shoulder Flexion/Abduction Test (170 degrees) and is evaluated. This test requires the patient's shoulder to be flexed and abducted in the same manner as the Active Prone Shoulder Flexion/Abduction Test. If a score of FN is given at step 439, then at step 466, the process moves to the TDN in motion process. If a score of DP or FP is given at step 439, then at step 472, the patient is diagnosed with pain, and is treated by applying the Passive Prone Shoulder Flexion/Abduction Test (170 degrees) to the TDN in motion process at step 445, as shown in FIG. 16. If a score of DN is given at step 439, then at step 442, the patient is diagnosed with Shoulder Flexion/Abduction TED, and is treated by applying the Passive Prone Shoulder Flexion/Abduction Test (170 degrees) to the TDN in motion process at step 445, as shown in FIG. 16. After TDN in motion is completed for step 445, the process continues to step 448.

At step 448, the patient executes the Active Prone Elbow Flexion Test (shoulder flexed). This test requires the patient to attempt to touch the thumb to the shoulder in the prone position with the arms and hands by the thighs while keeping the arm fully extended by the patient's side. If a score of FN is given at step 448, then at step 463, the process moves to the TDN in motion process. If a score of DN, DP, or FP is given at step 448, then the process continues to step 451.

At step 451, the patient executes the Passive Prone Elbow Flexion Test (shoulder flexed) and is evaluated. This test requires the patient's elbow to be flexed in the same manner as the Active Prone Elbow Flexion Test. If a score of FN is given at step 451, then at step 460, the process moves to the TDN in motion process. If a score of DP or FP is given at step 451, then at step 475, the patient is diagnosed with pain, and is treated by applying the Passive Prone Elbow Flexion Test to the TDN in motion process at step 457, as shown in FIG. 16. If a score of DN is given at step 451, then at step 454, the patient is diagnosed with Elbow Flex TED, and is treated by applying the Passive Prone Elbow Flexion Test to the TDN in motion process at step 457, as shown in FIG. 16. After completion of the TDN in motion process for step 457, the process continues to step 478.

At step 478, the patient executes an Active Lumbar Locked Extension (Chest) and is evaluated. This movement pattern requires a patient to enter a full prone rocking position, sitting on the calves with one forearm centered in front of the knees, and the other behind the back. The patient rotates the shoulder of the forearm that is behind the back, up and back as far as possible while maintaining the prone rocking position. If a score of FN is given at step 478, then at step 487, the process moves to the TDN in motion process. If a score of DP or FP is given at step 478, then at step 490, the patient is diagnosed with pain, and is treated by applying an Active Lumbar Locked Extension (Chest) movement pattern to the TDN in motion process at step 484, as shown in FIG. 16. If a score of DN is given at step 478, then at step 481, the patient is diagnosed with Thoracic Spine Extension TED or SMCD, and is treated by applying an Active Lumbar Locked Extension (Chest) to the TDN in motion process at step 484, as shown in FIG. 16.

FIG. 5 is flowchart 500 representing the steps involved in diagnosing whether a spine flexion movement pattern is painful, limited, or dysfunctional due to a myofascial trigger point, determining the target tissue to be treated, and determining the movement pattern to be used during treatment.

At step 505, the patient executes a Backward Bend without Upper Extremity ("UE") and is evaluated. This movement requires a patient to stand up straight and arch the body backwards with both hands on the hips. If a score of FN is given at step 505, then at step 565, the process moves to the TDN in motion process. If a score of DN, DP, or FP is given at step 505, then the process continues to step 510.

At step 510, the patient executes a Single Leg Backwards Bend and is evaluated. This movement requires a patient to stand up straight with both hands on the hips and arch the body backwards while standing on one leg. If a score of FN is given at step 510, then at step 550, the process moves to the TDN in motion process. If a score of DN, DP, or FP is given at step 510, then the process continues to step 515.

At step 515, the patient executes a Press Up and is evaluated. This movement requires a patient lying on the floor, facing the floor, to raise the body by pressing down on the hands while keeping the back straight. If a score of FN is given at step 515, then at step 555, the process moves to the TDN in motion process. If a score of DN, DP, or FP is given at step 515, then the process continues to step 520.

At step 520, the patient executes a Lumbar Locked (IR) Active Rotation/Extension (50 degrees) and is evaluated. This movement pattern requires a patient to enter a full prone rocking position, sitting on the calves with one forearm centered in front of the knees, and the other behind the back. The patient rotates the shoulder of the forearm that is behind the back, up and back as far as possible while maintaining the prone rocking position. If a score of FN is given at step 520, then at step 560, the process moves to the TDN in motion process. If a score of DN, DP, or FP is given at step 520, then the process continues to step 525.

At step 525, the patient executes a Lumbar Locked (IR) Passive Rotation/Extension (50 degrees) and is evaluated. This movement requires that the patient's lumbar be extended and rotated in the same manner as the Lumbar Locked IR Active Rotation/Extension. If a score of FN is given at step 525, then at step 545, the process moves to the TDN in motion process. If a score of FP or DP is given at step 525, then at step 570, the process moves to the next applicable movement pattern. If a score of DN is given at step 525, then the process continues to step 530, and a determination is made whether the DN is unilateral or bilateral. If it is determined at step 530 that the DN is bilateral, then at step 540, the patient is diagnosed with Thorax Bilateral Extension TED, and is treated by applying a Lumbar Locked (IR) Passive Rotation/Extension (50 degrees) to the TDN in motion process at step 535, as shown in FIG. 16. If a determination is made at step 530 that the DN is bilateral, then at step 575, the patient is diagnosed with Thorax Unilateral Extension TED, and is treated by applying a Lumbar Locked (IR) Passive Rotation/Extension (50 degrees) to the TDN in motion process at step 580, as shown in FIG. 16.

FIG. 6 is flowchart 600 representing the steps involved in diagnosing whether a lower body extension movement pattern is painful, limited, or dysfunctional due to a myofascial trigger point, determining the target tissue to be treated, and determining the movement pattern to be used during treatment. At step 610, the patient executes the FABER Test and is evaluated. This test requires that a patient's leg be flexed, and a corresponding thigh be abducted and externally rotated while the patient is lying down. If a score of FN is given at step 610, then at step 680, the process moves to the TDN in motion process. If a score of DN, DP, or FP is given the patient is diagnosed with Hip/Sacroiliac Joint TED and/or Core SMCD at step 620, and the therapist must use a standardize FABER to differentiate between the process. At step 630, Hip/Sacroiliac Joint TED and/or Core SMCD is treated by applying the FABER Test to the TDN in motion process. After completion of the TDN in motion process for step 630, the process continues to step 640.

At step 640 the patient executes the Modified Thomas Test and is evaluated. This test requires a patient to roll backwards while bringing the knees to the chest from a seated position on the edge of a treatment table. Next, one of the patient's legs is held in place. After that, the patient's non supported leg is then placed in 90 degrees of hip flexion and 90 degrees of knee flexion and is abducted next to the supporting leg. Then, the non-supported leg is then lowered with the patient placing zero tension in the leg as it is lowered. If a score of FN is given at step 640, then at step 670, the process moves to the TDN in motion process. If a score of DP, or FP is given at step 640, then at step 690, the process moves to the next applicable movement pattern. If a score of DN is given at step 640, then at step 650, the patient is diagnosed with Hip Extension TED and/or Core SMCD, and the therapist must perform local biomechanical testing of the hip to differentiate. At step 660, TDN in motion is used to treat Hip Extension TED and/or Core SMCD by applying the Modified Thomas Test to the TDN in motion process, as shown in FIG. 16.

FIG. 7 is flowchart 700 representing the steps involved in diagnosing whether a limited multi-segmental flexion movement pattern is painful, limited, or dysfunctional due to a myofascial trigger point, determining the target tissue to be treated, and determining the movement pattern to be used during treatment. At step 705, the patient executes a Single Leg Forward Bend and is evaluated. This movement requires a standing patient to cross the feet and reach for the toes without bending the back. If a score of FN is given at step 705, then at step 760, the process moves to the TDN in motion process. If a score of DN, DP, or FP is given at step 705, then the process continues to step 710.

At step 710, the patient executes a Long Sitting movement pattern and is evaluated. This movement requires a patient to sit with the legs fully extended forward and reach for the toes without bending the back. If a score of FN is given at step 710, then at step 755, the process moves to the TDN in motion process. If a score of DN, DP, or FP is given at step 710, then the process continues to step 715.

At step 715, the patient executes an Active Straight Leg Raise ("Active SLR") and is evaluated. This movement requires that a patient to raise a leg upwards while keeping it fully extended in the supine position. If a score of FN is given at step 715, then at step 750, the process moves to the TDN in motion process. If a score of DN, DP, or FP is given at step 715, then the process continues to step 720.

At step 720, the patient executes a Passive Straight Leg Raise ("Passive SLR") and is evaluated. This movement requires that a patient's leg be lifted in the same manner as the Active SLR movement. If a score of FN is given at step 720, at step 745, then the process moves to the TDN in motion process. If a score of DN, DP, or FP is given at step 720, then the process continues to step 725.

At step 725, the patient executes a Supine Knee to Chest movement pattern and is evaluated. This movement requires that a patient tuck the knees into the chest in the supine position. If a score of FN is given at step 725, then at step 740, the process moves to the TDN in motion process. If a score of FP or DP is given at step 720, then at step 765, the process moves to the next applicable movement pattern. If a score of DN is given at step 725, then at step 730, the patient is diagnosed with Posterior Chain TED, and is treated by applying a Supine Knee to Chest to the TDN in motion process at step 735, as shown in FIG. 16.

FIG. 8A-8B is flowchart 800 representing the steps involved in diagnosing whether an upper body extension movement pattern is painful, limited, or dysfunctional due to a myofascial trigger point, determining the target tissue to be treated, and determining the movement pattern to be used during treatment. At step 803, the patient executes a Unilateral Shoulder Backward Bend and is evaluated. This movement requires that a standing patient place one hand on a hip, extend the opposite arm vertically, and then arch the back. If a score of FN is given at step 803, then at step 833, the process moves to the TDN in motion process. If a score of DN, DP, or FP is given at step 803, then the process continues to step 806.

At step 806, the patient executes a Supine Lat Stretch with hips flexed is evaluated. This test requires the patient's knees to be brought to the chest while the patient is in the supine position with both arms held in 90 degrees of shoulder flexion and the palms facing each other. As the knees are brought to the chest the patient is required to lower the arms above the head and towards the floor while keep them fully extended. If a score of FN is given at step 806, then at step 830, the process moves to the TDN in motion process. If a score of DN, DP, or FP is given at step 806, then the process continues to step 809.

At step 809, the patient executes a Supine Lat Test with hips extended movement pattern and is evaluated. This test requires the patient's knees to be brought to the chest while the patient is in the supine position with both arms fully extended and held in front of the chest with the palms facing each other. As the knees are brought the chest, the patient is required to lower the arms above the head and towards the floor while keeping the arms fully extended and off the floor. Then, the patient's hips are extended to see if the arms drop to the floor. If a score of FN is given at step 809, then at step 827, the process moves to the TDN in motion process. If the therapist finds that the patient's shoulder flexion improved, but not fully, then at step 812, the patient is diagnosed with Lat/Posterior Chain TED. Then, at step 815, the Supine Lat Stretch with hips extended movement pattern is applied to the TDN in motion process to treat Posterior Chain TED, as shown in FIG. 16.

After the TDN in motion is complete for step 815, the process continues to step 818. Also, if a score of DN, DP, or FP was given at step 809, then the process continues to step 818.

At step 818 the patient executes a Lumbar Locked ER Unilateral Extension (50 degrees) and is evaluated. This movement pattern requires that a patient to go into a full prone rocking position, sitting on the calves with one forearm centered in front of the knees, and the other behind the head. The patient rotates the shoulder of the forearm that is behind the head, up and back as far as possible while maintaining the prone rocking position. If a score of FN is given at step 818, then at step 824, the process moves to the TDN in motion process. If a score of DN, DP, or FP is given at step 818, then the process continues to step 821.

At step 821, the patient executes a Lumbar Locked IR Active Rotation/Extension (50 degrees) and is evaluated. This movement pattern requires a patient to go into a full prone rocking position, sitting on the calves with one forearm centered in front of the knees, and the other behind the back. The patient rotates the shoulder of the forearm that is behind the back, up and back as far as possible while maintaining the prone rocking position. If a score of FN is given at step 821, then at step 848, the process moves to the TDN in motion process. If a score of DN, DP, or FP is given at step 821, then the process continues to step 836.

At step 836, the patient executes a Lumbar Locked IR Passive Rotation/Extension (50 degrees) and is evaluated. This movement requires that a patient's lumbar be rotated and extended in the same manner as the Lumbar Locked IR Active Rotation/Extension. If a score of FN, FP, or DP is given at step 836, then at step 845, the process moves to the TDN in motion process. If a score of DN is given only for one side at step 836, the patient is diagnosed with Thorax Unilateral Extension/Rotation TED at step 851, and is treated by applying a Lumbar Locked IR Passive Rotation/Extension (50 degrees) to the TDN in motion process at step 842, as shown in FIG. 16.

If a score of DN is given for both sides at step 836, the patient is diagnosed with Thorax Bilateral Extension/Rotation TED at step 839, and is treated by applying a Lumbar Locked IR Passive Rotation/Extension (50 degrees) to the TDN in motion process at step 842, as shown in FIG. 16.

FIG. 9 is flowchart 900 representing the steps involved in diagnosing whether a limited multi-segmental rotation is painful, limited, or dysfunctional due to a myofascial trigger point, determining the target tissue to be treated, and determining the movement pattern to be used during treatment. At step 905, the patient executes a Seated Rotation (50 degrees) and is evaluated. This movement requires the patient to hold a bar behind the back and rotate laterally while keeping the back straight in a seated position. If a score of FN is given at step 905, then at step 955, the process moves to the TDN in motion process. If a score of DN, FP, or DP is given at step 905, then the process continues to step 910.

At step 910, the patient executes a Lumbar Locked (ER) Unilateral Extension (50 degrees). This movement pattern requires a patient to go into a full prone rocking position, sitting on the calves with one forearm centered in front of the knees, and the other behind the head. The patient rotates the shoulder of the forearm that is behind the head, up and back as far as possible while maintaining the prone rocking position. If a score of FN is given at step 910, then at step 950, the process moves to the TDN in motion process. If a score of DN, FP, or DP is given at step 910, then the process continues to step 915. If a score of DN, FP, or DP is given at step 910, but switches sides, the patient executes the Rolling Patterns and is evaluated based on the outcome of FIG. 15. If a score of FN, FP, or DP is given at step 960, then at step 990, the process moves to the next applicable movement pattern. If a score of DN is given at step 960, the patient is diagnosed with Fundamental Rotational Pattern SMCD at step 965, and is treated by applying the Rolling Pattern that was scored DN on FIG. 15 to the TDN in motion process at step 970, as shown in FIG. 16.

At step 915 the patient executes a Lumbar Locked IR Active Rotation (50 degrees) and is evaluated. This movement pattern requires that a patient to go into a full prone rocking position, sitting on the calves with one forearm centered in front of the knees, and the other behind the back. The patient rotates the shoulder of the forearm that is behind the back, up and back as far as possible while maintaining the rocking prone position. If a score of FN is given at step 915, then at step 945, the process moves to the TDN in motion process. If a score of DN, DP, or FP is given at step 915, then the process continues to step 920.

At step 920, the patient executes a Lumbar Locked IR Passive Rotation (50 degrees) and is evaluated. This movement requires that a patient's lumbar be extended and rotated in the same manner as the Lumbar Locked IR Active Rotation/Extension. If a score of FN is given at step 920, then at step 940, the process moves to the TDN in motion process. If a score of FP or DP is given at step 920, then at step 975, the process moves to the next applicable movement pattern. If a score of DN is given at step 920, then at step 925, a determination is made whether the score of DN is unilateral or bilateral. If the score at step 925 is unilateral, then at step 980, the patient is diagnosed with Thorax Unilateral Rotation/Extension TED, and is treated by applying a Lumbar Locked IR Passive Rotation (50 degrees) to the TDN in motion process at step 985, as shown in FIG. 16.

If the score at step 925 is unilateral, then at step 935, the patient is diagnosed with Thorax Bilateral Rotation/Extension TED, and is treated by applying a Lumbar Locked IR Passive Rotation (50 degrees) to the TDN in motion process at step 930, as shown in FIG. 16.

FIG. 10 is flowchart 1000 representing the steps involved in diagnosing whether an external hip rotation movement pattern is painful, limited, or dysfunctional due to a myofascial trigger point, determining the target tissue to be treated, and determining the movement pattern to be used during treatment. At step 1005, the patient executes a Seated Active External Hip Rotation and is evaluated. This movement requires the patient to cross one foot over the other in a seated position on a table with both legs hanging shoulder width apart. If a score of FN at greater than 40 degrees is given at step 1005, then at step 1060, the process moves to the TDN in motion process. If a score of DN, DP, or FP is given at step 1005, then the process continues to step 1010.

At step 1010, the patient executes a Seated Passive External Hip Rotation and is evaluated. This movement requires that a patient's hip be rotated in the same manner as the Seated Active External Seated Hip Rotation. If a score of FN is given at step 1010, then at step 1055, the process moves to the TDN in motion process. If a score of FP or DP is given at step 1010, then at step 1065, the process moves to the next applicable movement pattern. If a score of DN is given at step 1010, then at step 1015, the patient is diagnosed with Hip TED with Extension Rotation and with Hip Flexed, and is treated by applying a Seated Passive External Hip Rotation to the TDN in motion process at step 1020, as shown in FIG. 16. After TDN in motion is complete for step 1020, the process continues to step 1025.

At step 1025 the patient executes a Prone Active External Hip Rotation. This movement requires the patient to bend one leg over the other leg as the other leg remains fully extended while the patient lies on a fitness ball in the prone position with the legs fully extended. If a score of FN at greater than 40 degrees is given at step 1025, then at step 1050, the process moves to the TDN in motion process. If a score of DN, DP, or FP is given at step 1025, then the process continues to step 1030.

At step 1030, the patient executes a Prone Passive External Hip Rotation and is evaluated. This movement requires that a patient's hip be rotated in the same manner as the Prone Active External Hip Rotation. If a score of FN is given at step 1030, then at step 1045, the process moves to the TDN in motion process. If a score of FP or DP is given at step 1030, then at step 1070, the process moves to the next applicable movement pattern. If a score of DN is given at step 1030, then at step 1035, the patient is diagnosed with Hip TED with Extension Rotation and with Hip Extended, and is treated by applying a Prone Passive External Hip Rotation to the TDN in motion process at step 1040, as shown in FIG. 16.

FIG. 11 is flowchart 1100 representing the steps involved in diagnosing whether an internal hip rotation movement pattern is painful, limited, or dysfunctional due to a myofascial trigger point, determining the target tissue to be treated, and determining the movement pattern to be used during treatment. At step 1105, the patient executes a Seated Active Internal Hip Rotation and is evaluated. This movement requires the patient to rotate one leg away from the other while the patient sits on a table with both feet hanging in the air shoulder width apart. If a score of FN at greater than 30 degrees is given at step 1105, then at step 1160, the process moves to the TDN in motion process. If a score of DN, DP, or FP is given at step 1105, then the process continues to step 1110.

At step 1110, the patient executes a Seated Passive Internal Hip Rotation and is evaluated. This movement requires that a patient's hip be rotated in the same manner as the Seated Active Internal Hip Rotation. If a score of FN is given at step 1110, then at step 1155, the process moves to the TDN in motion process. If a score of FP or DP is given at step 1110, then at step 1165, the process moves to the next applicable movement pattern. If a score of DN is given at step 1110, then at step 1115, the patient is diagnosed with Hip TED with Medial Rotation and with Hip Flexed, and is treated by applying a Seated Passive Internal Hip Rotation to the TDN in motion process at step 1120, as shown in FIG. 16. After TDN in motion is completed for step 1120, then the process continues to step 1125.

At step 1125 the patient executes a Prone Active Internal Hip Rotation and is evaluated. This movement requires the patient to bend one leg in the opposite direction of the other leg while the patient lies on a fitness ball in the prone position with the legs fully extended. If a score of FN at greater than 30 degrees is given at step 1125, then at step 1150, the process moves to the TDN in motion process. If a score of DN, DP, or FP is given at step 1125, then the process continues to step 1130.

At step 1130, the patient executes a Prone Passive Internal Hip Rotation and is evaluated. This movement requires that the patient's hip be rotated in the same manner as the Prone Active Internal Hip Rotation. If a score of FN is given at step 1130, then at step 1145, the process moves to the TDN in motion process. If a score of FP or DP is given at step 1130, then at step 1170, the process moves to the next applicable movement pattern. If a score of DN is given at step 1130, then at step 1135, the patient is diagnosed with Hip TED with Med. Rotation and with Hip Extended, and is treated by applying a Prone Passive Internal Hip Rotation to the TDN in motion process at step 1140, as shown in FIG. 16.

FIG. 12A is flowchart 1200 representing the steps involved in diagnosing whether an internal tibial movement pattern is painful, limited, or dysfunctional due to a myofascial trigger point, determining the target tissue to be treated, and determine the movement pattern to be used during treatment. At step 1205 the patient executes a Seated Active Internal Tibial Rotation and is evaluated. This test requires a patient to internally rotate one foot towards the other foot from a seated position while maintaining an erect and upright posture with the arms at the patient's side and the knees flexed 90 degrees. If a score of FN is given at step 1205, then at step 1230, the process moves to the TDN in motion process. If a score of DN, DP, or FP is given at step 1205, then the process continues to step 1210.

At step 1210, the patient executes a Seated Passive Internal Tibial Rotation and is evaluated. This test requires the patient's foot to be rotated in the same manner as the Seated Passive Internal Rotation Test. If a score of FN is given at step 1210, then at step 1225, the process moves to the TDN in motion process. If a score of FP or DP is given at step 1210, then at step 1235, the process moves to the next applicable movement pattern. If a score of DN is given at step 1210, then at step 1215, the patient is diagnosed with Tibial Internal Rotation TED, and is treated by applying a Seated Passive Internal Tibial Rotation to the TDN in motion process at step 1220, as shown in FIG. 16.

FIG. 12B is a flowchart representing the steps involved in diagnosing whether an external tibial rotation movement pattern is painful, limited, or dysfunctional due to a myofascial trigger point, determining the target tissue to be treated, and determining the movement pattern to be used during treatment. At step 1240, the patient executes a Seated Active External Tibial Rotation and is evaluated. This test requires a patient to externally rotate one foot away the other foot in a seated position while maintaining an erect and upright posture with the arms at the patient's side and the knees flexed 90 degrees. If a score of FN is given at step 1240, then at step 1265, the process moves to the TDN in motion process. If a score of DN, DP, or FP is given at step 1240, then the process continues to step 1245.

At step 1245, the patient executes a Seated Passive External Tibial Rotation and is evaluated. This test requires the patient's foot to be rotated in the same manner as the Seat Passive External Tibial Rotation Test. If a score of FN is given at step 1245, then at step 1260, the process moves to the TDN in motion process. If a score of FP or DP is given at step 1245, then at step 1270, the process moves to the next applicable movement pattern. If a score of DN is given at step 1245, then at step 1250, the patient is diagnosed with Tibial External Rotation TED, and is treated by applying a Seated Passive External Tibial Rotation to the TDN in motion process at step 1255, as shown in FIG. 16.

FIG. 13A-B is flowchart 1300 representing the steps involved in diagnosing whether an ankle movement pattern is painful, limited, or dysfunctional due to a myofascial trigger point, determining the target tissue to be treated, and determining the movement pattern to be used during treatment. At step 1303, the patient executes Heel Walks and is evaluated. This movement requires that a patient walks with only the heels contacting the floor. If a score of FN is given at step 1303, then at step 1336, the process moves to the TDN in motion process. If a score of DN, DP, or FP is given at step 1303, then the process continues to step 1306.

At step 1306, the patient executes a Prone Passive Dorsiflexion and is evaluated. This movement requires that a patient's foot be flexed upwards in the prone position. If a score of FN is given at step 1306, then at step 1333, the process moves to the TDN in motion process. If a score of DP or FP is given at step 1306, then at step 1339, the patient is diagnosed with pain. At step 1312, the pain is treated by applying a Prone Passive Dorsiflexion to the TDN in motion process, as shown in FIG. 16. If a score of DN is given at step 1306, then at step 1309, the patient is diagnosed with Lower Posterior Chain TED, and is treated by applying a Prone Passive Dorsiflexion to the TDN in motion process at step 1312, as shown in FIG. 16. After the TDN in motion Process is complete for step 1312, the process continues to step 1315.

At step 1315, the patient executes Toe Walks and is evaluated. This movement requires that a patient walks with only the toes contacting the floor. If a score of FN is given at step 1315, then at step 1330, the process moves to the TDN in motion process. If a score of DN, DP, or FP is given at step 1315, then the process continues to step 1318.

At step 1318, the patient executes a Prone Passive Plantar Flexion and is evaluated. This movement requires the patient's foot to be flexed downwards while the patient is in the prone position. If a score of FN is given at step 1318, then at step 1327, the process moves to the TDN in motion process. If a score of DP or FP is given at step 1318, then at step 1342, the patient is diagnosed with pain. At step 1324, the pain is treated by applying a Prone Passive Plantar Flexion to the TDN in motion process, as shown in FIG. 16. If a score of DN is given at step 1318, then at step 1321, the patient is diagnosed with Lower Anterior Chain TED, and is treated by applying a Prone Passive Plantar Flexion to the TDN in motion process at step 1324, as shown in FIG. 16. After the TDN in motion process is completed for step 1324, then the process continues to step 1345.

At step 1345 the patient executes a Seated Active Ankle Inversion/Eversion and is evaluated. This movement requires that a patient to rolls the ankle in the lateral, or outward direction, and the medial, or inward, direction in the seated position. If a score of FN is given at step 1345, then at step 1360, the process moves to the TDN in motion process. If a score of DN, FP, or DP is given at step 1345, then the process continues to step 1348.

At step 1348, the patient executes a Seated Passive Ankle Inversion/Eversion and is evaluated. This movement requires that a patient's foot to be inverted and everted in the same manner as Seated Active Ankle Inversion/Eversion. If a score of FN is given at step 1348, then at step 1357, the process moves to the TDN in motion process. If a score of DP or FP is given at step 1348, then at step 1363, the process moves to the next applicable movement pattern. If a score of DN is given at step 1348, at step 1351, the patient is diagnosed with Ankle (Eversion or Inversion) TED, and is treated by applying a Seated Passive Ankle Inversion/Eversion to the TDN in motion process at step 1354, as shown in FIG. 16.

FIG. 14 is flowchart 1400 representing the steps involved in diagnosing whether a limited overhead deep squat movement is painful, limited, or dysfunctional due to a myofascial trigger point, determining the target tissue to be treated, and determining the movement pattern to be used during treatment. At step 1405, the patient executes an Interlocked Fingers behind Neck Deep Squat and is evaluated. This movement requires that a patient with the fingers interlocked behind the head, to stand with the feet slightly wider than the hips with the toes pointed slightly outward. Then the patient squats down keeping the back straight and the knees in line with the feet until the hip joint drops below the knees. Then the patient stands back up. If a score of FN is given at step 1405, then at step 1460, the process moves to the TDN in motion process. If a score of DN, FP, or DP is given at step 1405, then the process continues to step 1410.

At step 1410, the patient executes an Assisted Squat and is evaluated. This test requires a patient to squat while the patient's arms are extended and the hands are held for support. If a score of FN is given at step 1410, then at step 1455, the process moves to the TDN in motion process. If a score of DN, FP, or DP is given at step 1410, then the process continues to step 1415. At step 1415, the patient executes a half kneeling dorsiflexion. Dorsiflexion is the backward bending of the hand or foot. If a score of DN is given, then at step 1465 the patient is diagnosed with lower posterior chain TED, and is then treated by the TDN in motion process at step 1470. If a score of FN is given, then the process moves to step 1450 and the TDN in motion process. If a score of FP or DP is given then the process moves to step 1420.

At step 1420, the patient executes a Supine Knees to Chest Holding Shins and is evaluated. This movement requires the patient to bring the knees to the chest while holding onto the shins in the supine position. If a score of FN is given at step 1420, then at step 1445, the process moves to the TDN in motion process. If a score of DN, FP, or DP is given at step 1420, then the process continues to step 1425.

At step 1425, the patient executes a Supine Knees to Chest Holding Thighs. This movement requires that a patient brings the knees to the chest while holding onto the thighs in the supine position. If a score of FN is given at step 1425, then at step 1440, the process moves to the TDN in motion process. If a score of FP or DP is given at step 1425, then at step 1475, the process moves to the next applicable movement pattern. If a score of DN is given at step 1420, then at step 1430, the patient is diagnosed with Lower Anterior TED, and is treated by applying a Supine Knees to Chest Holding Thighs to the TDN in motion process at step 1435, as shown in FIG. 16.

FIG. 15 is flowchart 1500 representing the Rolling Pattern Outcomes as shown in FIG. 9. At step 960, the scores are based on the outcome of the Rolling Patterns.

At step 1505, the patient executes a Prone to Supine Roll with Upper Body and is evaluated. This movement pattern requires a patient lying on the stomach, to roll over onto the back with both arms extended. If a score of DP or FP is given at step 1505, then at step 1550 that score will be used as the outcome of step 960. If a score of FN is given at step 1505, then at step 1545 that score will be used as the outcome of step 960. If a score of DN is given at step 1505, then the process continues to step 1510.

At step 1510, the patient executes Prone to Supine Rolling with Lower Body. This movement pattern requires that a patient lying on the stomach with one leg raised in the air to roll over onto the back in the direction of the leg on the floor. If a score of DP or FP is given at step 1510, then at step 1555 that score will be used as the outcome of step 960. If a score of FN is given at step 1510, then at step 1540 that score will be used as the outcome of steps 960 and 1330. If a score of DN is given at step 1510, then the process continues to step 1515.

At step 1515, the patient executes Supine to Prone Roll with Upper Body and is evaluated. This movement pattern requires that a patient lying on the back to roll over onto the stomach with both arms extended. If a score of DP or FP is given at step 1515, at step 1560 that score will be used as the outcome of step 960. If a score of FN is given at step 1515, then at step 1535 that score will be used as the outcome of step 960. If a score of DN is given at step 1515, then the process continues to step 1520.

At step 1520, the patient executes Supine to Prone Rolling with Lower Body. This movement pattern requires that a patient lying on the back with one leg raised in the air to roll over onto the stomach in the direction of the leg on the floor. If a score of DP or FP is given at step 1520, then at step 1565 that score will be used as the outcome of step 960. If a score of FN is given at step 1520, then at step 1530 that score will be used as the outcome of steps 960 and 1330. If a score of DN is given at step 1520, then at step 1525 that score will be used as the outcome of step 960.

FIG. 16 shows a flowchart representing a preferred embodiment of the TDN motion process 1600. At step 1605, the patient's range of movement is assessed and noted. At step 1610, the needle is inserted into the target tissue, along the prescribed entry axis, with the patient in the beginning position of the patient movement pattern. At step 1615, the patient begins the movement as the needle stays inserted in the target tissue at the entry angle. At step 1620, the needle is moved according to a predetermined first protocol as the patient executes the patient movement pattern. The patient movement pattern executed is the one conducted immediately before beginning the TDN motion process. At step 1621, an evaluation is made as to whether or not LTR has been induced. If not, the method moves to step 1622 and the next needle movement protocol is chosen, as will be further described. The method then returns to step 1615. If so, the method proceeds to step 1625.

In another preferred embodiment of the method, if LTR is not induced at step 1621, then the method proceeds to step 1625. In this preferred embodiment, LTR is necessary only at step 1636. For this reason, the same needle movement protocol is used to evaluate LTR at step 1636.

At step 1625, the movement pattern is continued until a new upper limit of the patient's range of movement is reached. At step 1630, the patient reverses the patient movement pattern as the needle stays inserted in the target tissue. At step 1635, the needle is moved according to a second predetermined protocol as the patient reverses the movement pattern. The method then moves to step 1636. At step 1636, a decision is made as to whether or not LTR has been induced. If not, the method moves to step 1637 where a next needle movement protocol is chosen, as will be further described. The method then returns to step 1630. If so, the method moves to step 1640.

In another preferred embodiment, if LTR has been induced at step 1637, then if LTR is not induced at step 1636 the method moves to step 1640. In this preferred embodiment, LTR is necessary at step 1621.

At step 1640, the patient continues the patient movement pattern until the beginning position is reached. At step 1645, the needle is removed.

At step 1650, the patient is evaluated for an acceptable range of motion. At step 1650, the same movement pattern is retested to evaluate range of movement. If the patient has reached an acceptable range of movement, then, the method moves to step 1655. If not, then the method returns to step 1605. At step 1655, it is determined whether or not all target tissues have been treated. If all target tissues have been treated, then the process moves to step 1660 and concludes. If not, then the method moves to step 1670 where the next target tissue location is chosen. The method then returns to step 1605.

Figure 17A:
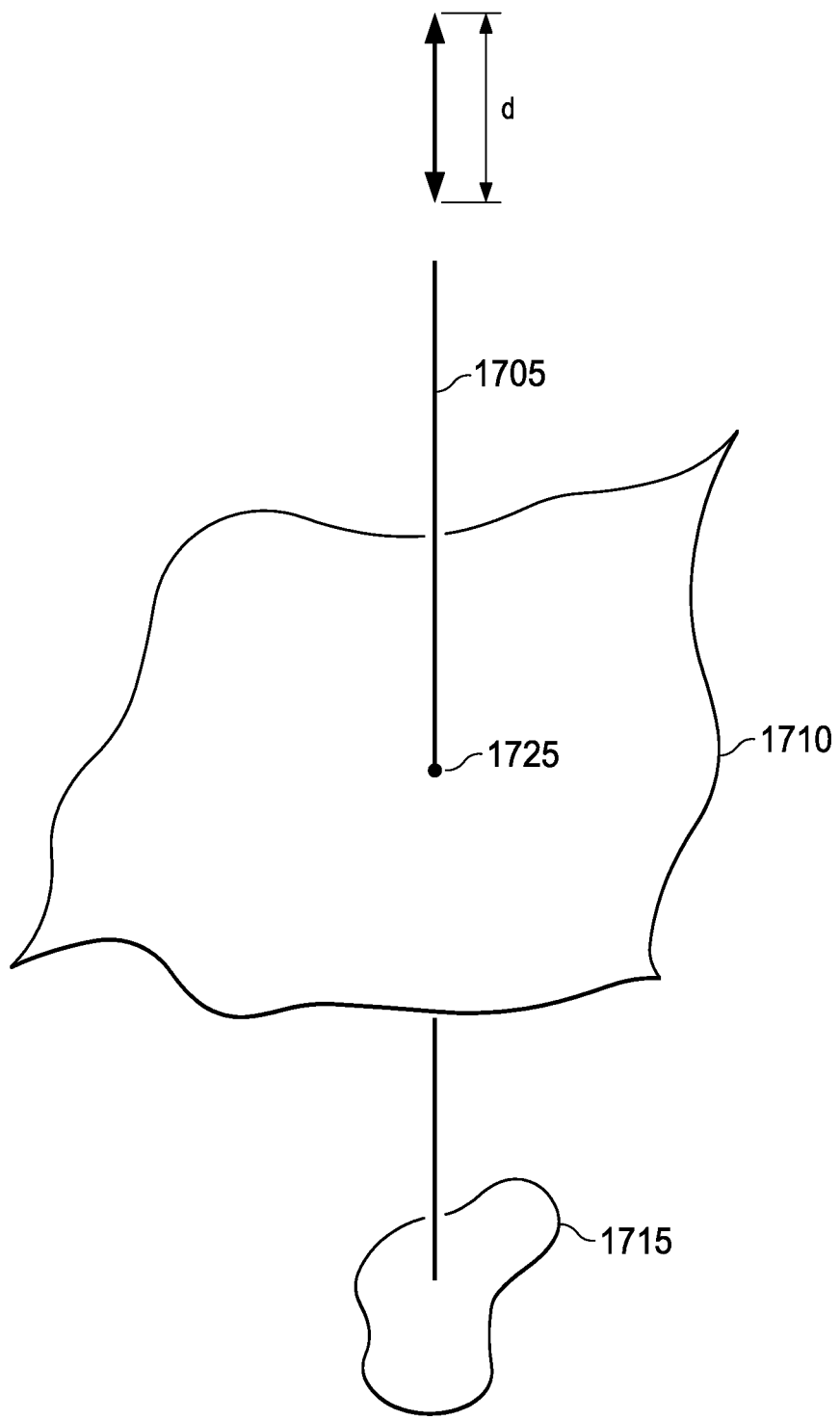
FIG. 17A is an isometric view of a preferred embodiment of a needle movement protocol.
Figure 17B:
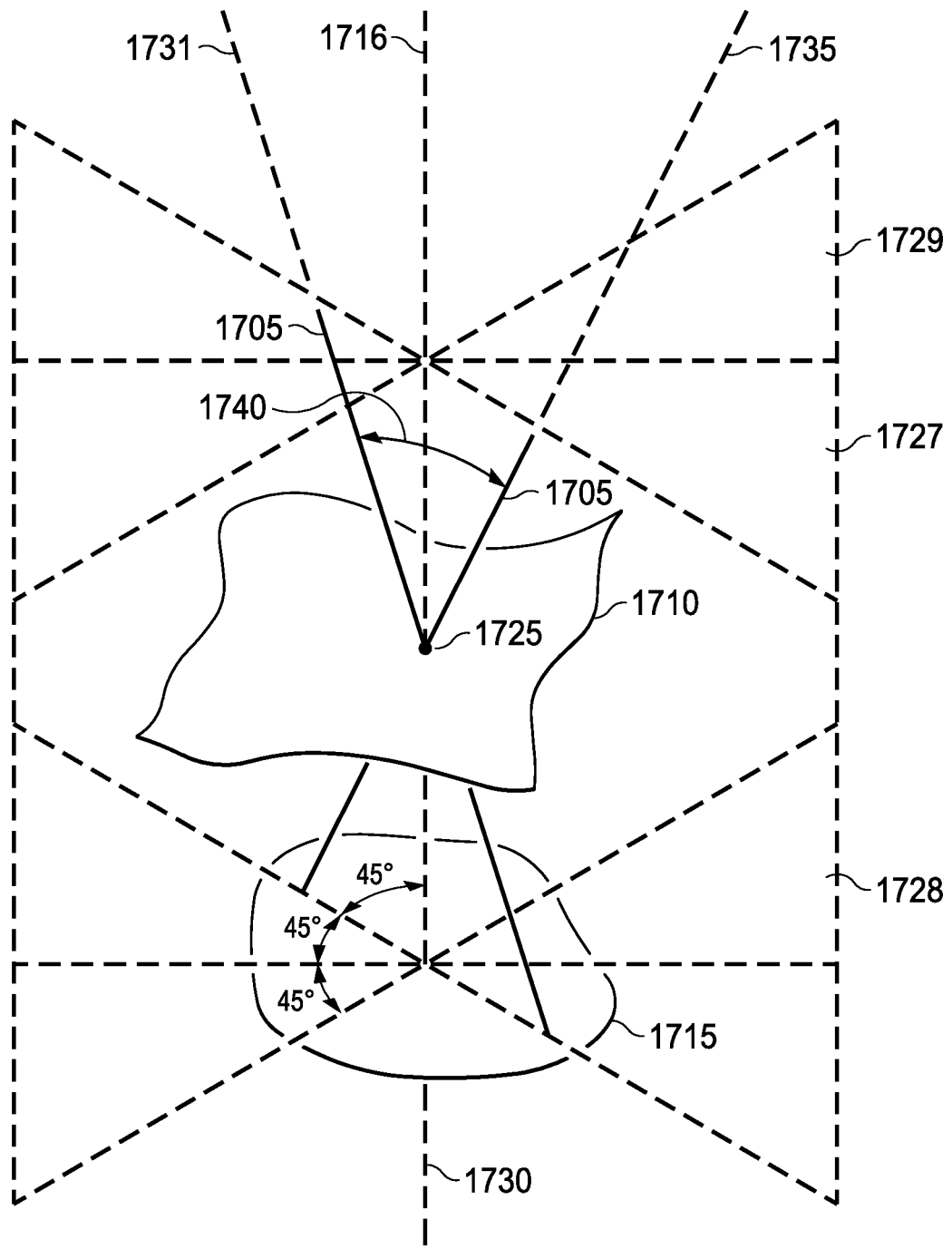
FIG. 17B is an isometric view of a preferred embodiment of a needle movement protocol.

Referring to FIG. 17A, a "piston" needle movement protocol is described. In a preferred embodiment, needle 1705 is inserted through skin 1710, at predefined axis 1716, through the insertion point 1725 and into myofascial trigger point 1715. The needle is then moved axially through distance "d", known as needle "amplitude". The motion is then reversed creating a motion sequence. The needle motion sequence is repeated at a predefined frequency for the duration of a specified patient motion. A preferred embodiment of needle amplitude and frequency is shown in FIG. 18A in columns 1855 and 1860. Please amend the specification as follows:

Referring to FIG. 17B, a "fan" needle movement protocol is described. Needle 1705 is inserted through skin 1710 at insertion point 1725 and into myofascial trigger point 1715, along axis 1716. As the patient executes a patient movement sequence, needle 1705 is rotated in a chosen plane 1727, about insertion point 1725 between needle positions 1731 and 1735. The distance between needle positions 1731 and 1735 is determined by predefined "amplitude" angle 1740. The needle motion sequence is repeated at a predetermined frequency for the duration of a specified patient motion sequence. The protocol may also require a change to the needle movement to planes 1727, 1728, 1729, and 1730. In a preferred embodiment, each of planes 1727, 1728, 1729, and 1730 intersect at axis 1716 and are located at approximately 45° angles relative to each other, within a 4° to 5° tolerance. Plane 1730 is shown perpendicular to the page. Predefined amplitude angle 1740, and predetermined frequency examples are shown in columns 1865 and 1870 of FIG. 18B.

Figure 17C:
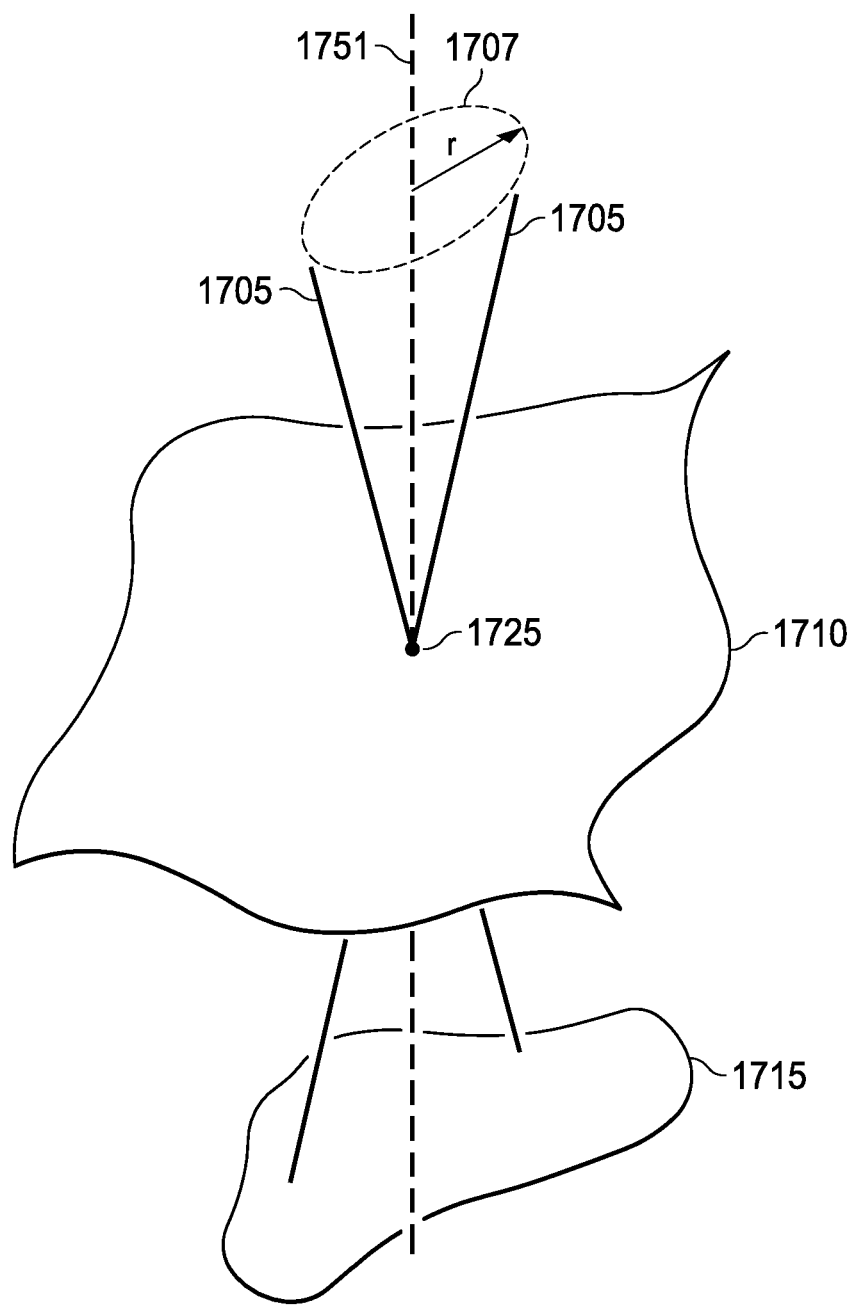
FIG. 17C is an isometric view of a preferred embodiment of a needle movement protocol.

Referring to FIG. 17C, a "rotation" needle movement protocol is described. Needle 1705, is inserted into skin 1710 at insertion point 1725, along axis 1751, and into myofascial trigger point 1715. As the patient executes the patient movement pattern, needle 1705 is moved in a conical pattern 1707 about axis 1751, with an apex at insertion point 1725, at a predefined amplitude angle 1740 and frequency. The amplitude of the needle movement is defined by radius "r". Preferred examples of predetermined amplitude and predetermined frequency are shown in columns 1875 and 1880 in FIG. 18C.

Figure 17D:
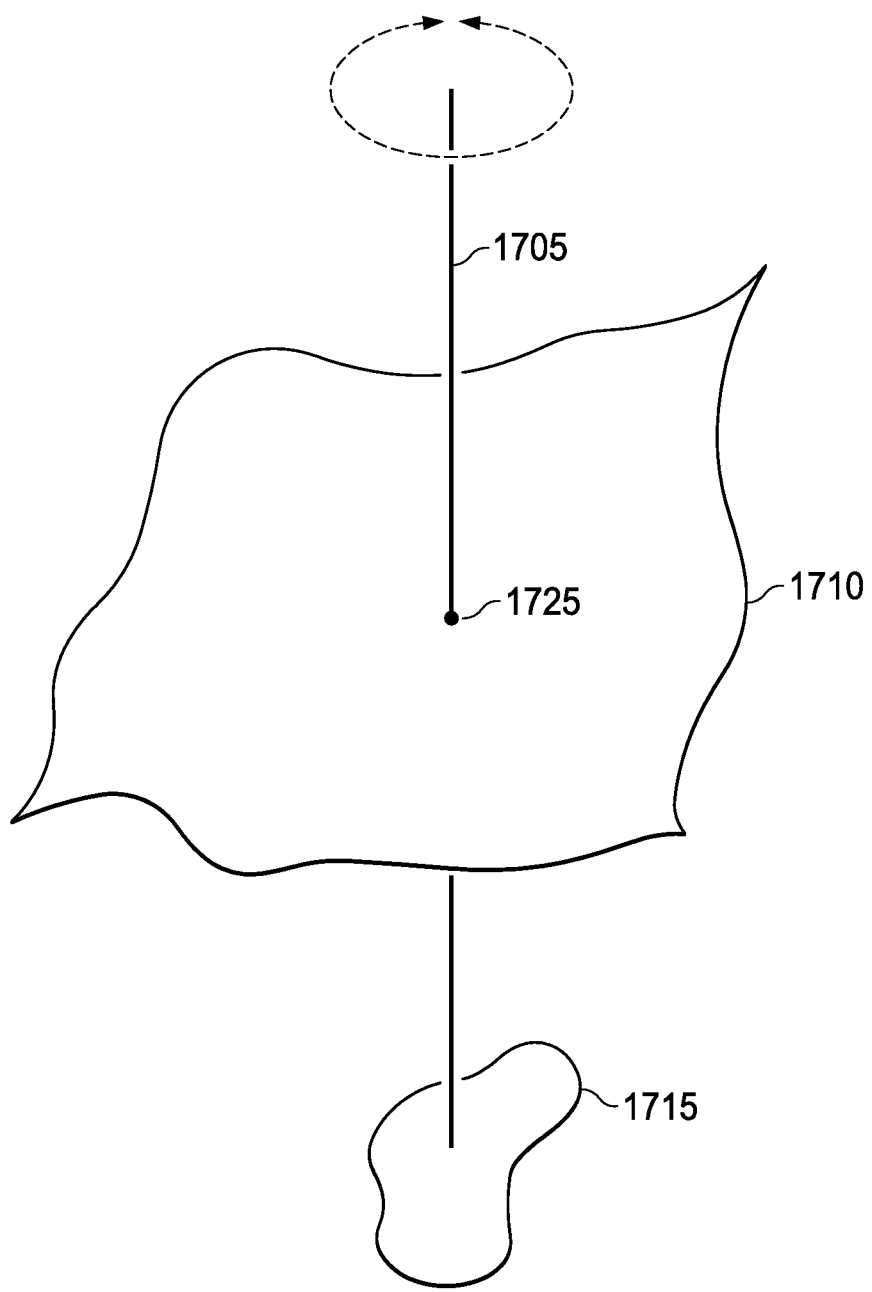
FIG. 17D is an isometric view of a preferred embodiment of a needle movement protocol.

Referring then to FIG. 17D, a "twist" needle movement protocol is described. Needle 1705 is inserted into skin 1710 at an insertion point 1725 and into myofascial trigger point 1715 at axis 1716. As the patient executes the instructed patient movement pattern, needle 1705 is rotated 360° clockwise and then rotated 360° counterclockwise about its longitudinal axis. A preferred set of frequencies for the "twist" needle movement protocol is 1, 2, 3, 4, and 5 cycles per second.

FIG. 18A shows a table of amplitudes and frequencies for a preferred embodiment of the "piston" needle movement protocol. Column 1855 contains the amplitudes that can be selected to be used as needle amplitude 1720 during the vertical needle movement protocol. Column 1860 defines the frequency, which is the required number of needle movements per second that must be made during patient movement based on the amplitude.

FIG. 18B shows a table of amplitudes and frequencies for a preferred embodiment of the "fan" needle movement protocol. Column 1865 contains the amplitudes that can be selected to be used as predefined amplitude 1740 during the fanning needle movement protocol. Column 1870 defines the frequency, which is the required number of needle movements per second that must be made during patient movement based on the amplitude.

FIG. 18C shows a table of amplitudes and frequencies for a preferred embodiment of the "rotation" needle movement protocol. Column 1875 identifies values for the amplitude used during preferred embodiment of the rotational needle movement protocol. Column 1880 identifies frequency used during a preferred embodiment of the rotational needle movement protocol of a preferred embodiment. The "frequency" is the required number of needle movements per second that must be made during patient movement.

Figure 19:
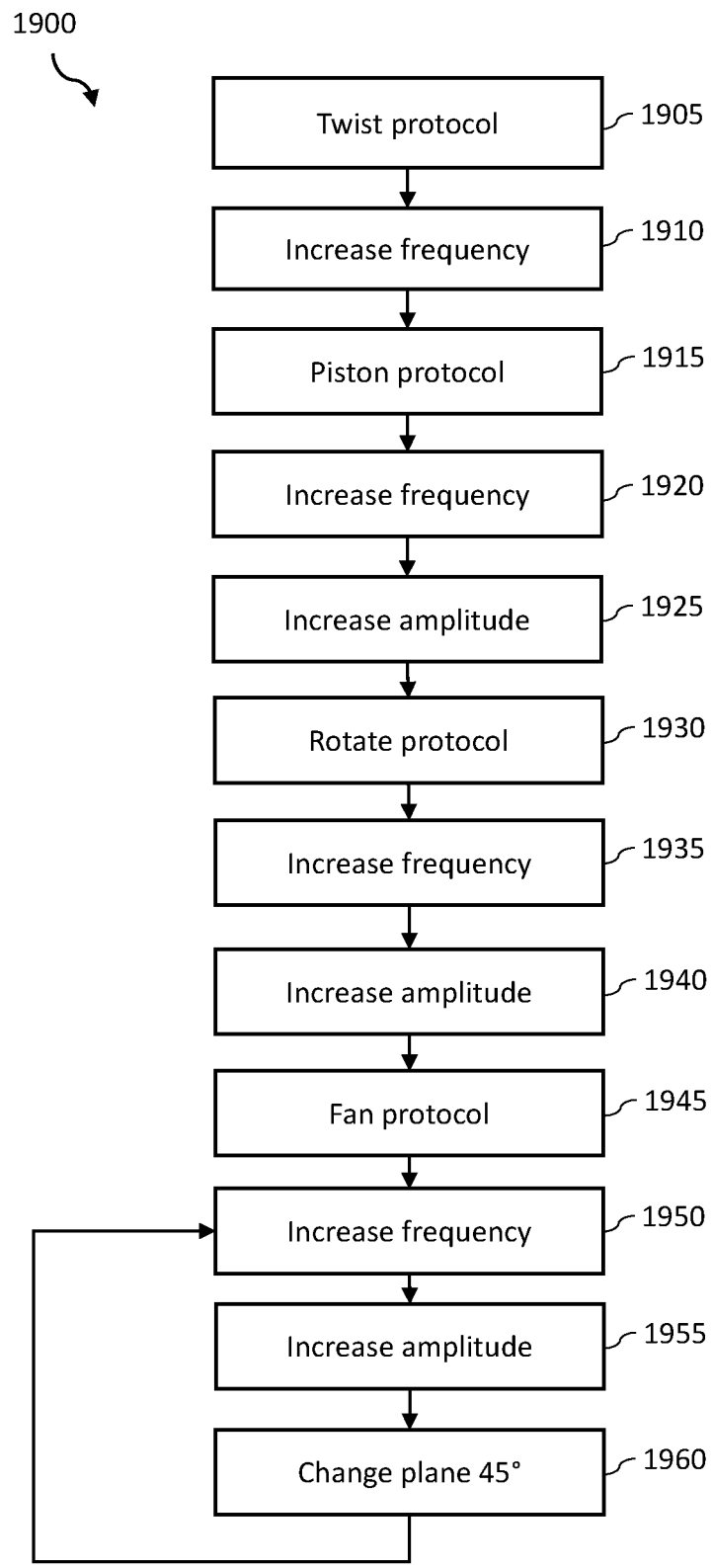
FIG. 19 is a flow chart of a preferred embodiment of a needle protocol selection schedule.

Referring then to FIG. 19, a preferred embodiment of the needle movement protocol schedule 1900 is described. In general, the goal of the needle movement protocol schedule is to advance through a set of needle movement protocols in an orderly fashion, during treatment to achieve an LTR with the least amount of potential tissue damage.

At step 1905, the "twist" needle movement protocol is used at a minimum prescribed frequency. If no LTR is received, then at step 1910 the "twist" protocol frequency is increased according to a prescribed rate. If no LTR is received, then the schedule moves to step 1915 and employs a piston protocol at a predetermined initial frequency, and if no LTR is received, then at step 1920 the frequency is increased according to a prescribed table. If upon reaching the maximum piston frequency, no LTR is induced, then at step 1925 the amplitude of the piston movement is increased according to a prescribed table, until LTR is induced.

If no LTR is induced, then the schedule moves to step 1930 and employs a "rotate" protocol induced at a predefined initial frequency. If no LTR is induced, then at step 1935, the rotation frequency is increased according to a prescribed table. If upon reaching the maximum rotation frequency, no LTR is induced, then at step 1940 the amplitude of the rotation movement is increased according to a prescribed table until LTR is induced.

If no LTR response is received, then the schedule moves to step 1945 and employs a "fan" protocol and initially sets a minimum frequency. If no LTR is induced, then the frequency is increased at step 1950 according to a prescribed table. If upon reaching the maximum fan frequency, no LTR is induced, then at step 1955 the amplitude of the fan movement is increased according to a prescribed table. If no LTR is induced then, at step 1960, the plane of the needle movement is advanced 45° in a clockwise direction and the method returns to step 1950. Steps 1950, 1955, and 1960 are repeated until LTR is induced.

FIG. 20 comprises of a chart of preferred needle diameters that can be selected to be used during the TDN motion process. According to the table, needle diameter is chosen according to the depth of the target tissue from the skin surface.

The invention claimed is:

1. A method for treating a limited, painful, or dysfunctional movement comprising:
    observing a first performance of a first patient movement pattern;
    identifying a target tissue based on the observation;
    inserting a needle into the target tissue to a myofascial trigger point and executing a trigger point dry needling movement protocol;
    performing the trigger point dry needling movement protocol while a second performance of the first patient movement pattern is being performed; and,
    if a local twitch response is not induced during the second performance of the first patient movement pattern, then changing the trigger point dry needling movement protocol.

2. The method of claim 1, wherein the step of observing further comprises:
    observing a beginning position, a forward movement pattern, an ending position, and a reverse movement pattern.

3. The method of claim 2, further comprising:
    inserting the needle into the target tissue to the myofascial trigger point with the patient in the beginning position.

4. The method of claim 2, further comprising:
    observing the forward movement pattern until a limit in motion is reached; and,
    defining the ending position as the limit in motion.

5. The method of claim 4, further comprising:
    observing the second performance of the first patient movement pattern while the needle movement protocol is being performed.

6. The method of claim 1, further comprising:
    using a twist protocol with a twist frequency as the needle movement protocol until the local twitch response is induced; and,
    if the local twitch response is not induced, then increasing the twist Frequency until the local twitch response is induced or until the second performance of the first patient movement pattern is complete.

7. The method of claim 6, further comprising:
    if the local twitch response is not induced with the twist protocol then using a piston protocol with a piston frequency and a piston amplitude as the needle movement protocol until the local twitch response is induced or until a third performance of the first patient movement pattern is complete.

8. The method of claim 7, further comprising:
    if the local twitch response is not induced with the piston frequency, then progressively increasing the piston frequency until the local twitch response is induced; and,
    if the local twitch response is not induced with the piston amplitude, then progressively increasing the piston amplitude until the local twitch response is induced.

9. The method of claim 8, further comprising:
    if the local twitch response is not induced with the piston protocol, then using a rotate protocol with a rotate frequency and a rotate amplitude as the needle movement protocol until the local twitch response is induced or until a fourth performance of the first patient movement pattern is complete.

10. The method of claim 9, further comprising:
    if the local twitch response is not induced with the rotate frequency, then progressively increasing the rotate frequency until the local twitch response is induced; and,
    if the local twitch response is not induced with the rotate amplitude. then progressively increasing the rotate amplitude until the local twitch response is induced.

11. The method of claim 10, further comprising:
    if the local twitch response is not induced with the piston protocol, then using a rotate protocol with a rotate frequency and a rotate amplitude as the needle movement protocol until the local twitch response is induced or until a fifth performance of the first patient movement pattern is complete.

12. The method of claim 11, further comprising:
    if the local twitch response is not induced with the rotate frequency, then progressively increasing the rotate frequency until the local twitch response is induced; and,
    if the local twitch response is not induced with the rotate amplitude then progressively increasing the rotate amplitude until the local twitch response is induced.

13. The method of claim 12, further comprising:
    if the local twitch response is not induced with the rotate protocol, then using a fan protocol with a fan frequency and a fan amplitude as the needle movement protocol until the local twitch response is induced or until a sixth performance of the first patient movement pattern is complete.

14. The method of claim 13, further comprising:
    if the local twitch response is not induced with the rotate protocol, then progressively increasing the fan frequency until the local twitch response is induced; and,
    if the local twitch response is not induced with the fan amplitude, then progressively increasing the fan amplitude until the local twitch response is induced.

15. The method of claim 14, further comprising:
    wherein the fan protocol includes a first plane of needle movement; and,
    if the local twitch response is not induced with the first plane of needle movement, then repeating the fan protocol with a second plane of needle movement.

16. The method of claim 1, further comprising:
    assessing an initial motion range based on the observation.

17. The method of claim 1, further comprising:
    before the step of inserting, assigning a score based on the observation that is selected from the group of functional non-painful, functional painful, dysfunctional non-painful, and dysfunctional painful.

18. The method of claim 17, further comprising:
    ending a sequence of movement patterns if a score of functional non-painful is assigned.

19. A method of treating a patient comprising the steps of:
choosing a first patient movement pattern;
observing an execution of the first patient movement pattern;
during the execution of the first patient movement pattern, accessing whether an FP, FN, DP, DN, SMCD, or TED condition is present;
accessing an initial patient motion range;
locating a target tissue;
choosing a primary trigger point dry needling movement protocol;
choosing a secondary trigger point dry needling movement protocol;
choosing a second patient movement pattern;
performing a trigger point dry needling procedure on the target tissue with the primary trigger point dry needling movement protocol and the secondary trigger point dry needling movement protocol during execution of the first patient movement pattern and the second patient movement pattern; and,
evaluating a resulting patient motion range.

20. The method of claim 19 further comprises the steps of:
moving the needle according to the primary trigger point dry needling movement protocol until a first LTR is induced; and,
moving the needle according to the secondary trigger point dry needling movement protocol until a second LTR is induced.

21. The method of claim 19 wherein the primary trigger point dry needling movement protocol and the secondary trigger point dry needling movement protocol are different.

* * * * *